(12) United States Patent
Hagting et al.

(10) Patent No.: US 11,291,625 B2
(45) Date of Patent: Apr. 5, 2022

(54) ANTIMICROBIAL COMPOSITIONS AND METHODS FOR REDUCING MICROBIAL CONTAMINATION

(71) Applicant: PolyVation B.V., Groningen (NL)

(72) Inventors: Joke Geesje Hagting, Groningen (NL); Theodorus Adrianus Cornelius Flipsen, Groningen (NL); Herbert Wilhelm Ulmer, Groningen (NL)

(73) Assignee: PolyVation B.V., Groningen (NL)

( * ) Notice: Subject to any disclaimer, the term of this patent is extended or adjusted under 35 U.S.C. 154(b) by 197 days.

(21) Appl. No.: 15/571,647

(22) PCT Filed: May 6, 2016

(86) PCT No.: PCT/NL2016/050326
§ 371 (c)(1),
(2) Date: Nov. 3, 2017

(87) PCT Pub. No.: WO2016/178578
PCT Pub. Date: Nov. 10, 2016

(65) Prior Publication Data
US 2018/0147137 A1 May 31, 2018

(30) Foreign Application Priority Data
May 6, 2015 (EP) .................................. 15166652

(51) Int. Cl.
| | | |
|---|---|---|
| *A61K 9/00* | (2006.01) | |
| *A01N 25/10* | (2006.01) | |
| *A61K 47/32* | (2006.01) | |
| *A01N 25/02* | (2006.01) | |
| *A61Q 17/00* | (2006.01) | |
| *A61K 8/11* | (2006.01) | |
| *A61K 8/41* | (2006.01) | |
| *A61K 8/90* | (2006.01) | |
| *A01N 33/12* | (2006.01) | |
| *A01N 39/00* | (2006.01) | |
| *A01N 47/44* | (2006.01) | |

(52) U.S. Cl.
CPC ............ *A61K 9/0014* (2013.01); *A01N 25/02* (2013.01); *A01N 25/10* (2013.01); *A61K 8/11* (2013.01); *A61K 8/416* (2013.01); *A61K 8/90* (2013.01); *A61K 47/32* (2013.01); *A61Q 17/00* (2013.01); *A61Q 17/005* (2013.01); *A01N 33/12* (2013.01); *A01N 39/00* (2013.01); *A01N 47/44* (2013.01); *A61K 2800/56* (2013.01)

(58) Field of Classification Search
USPC ...................................................... 424/405
See application file for complete search history.

(56) References Cited

FOREIGN PATENT DOCUMENTS

| | | | |
|---|---|---|---|
| EP | 0164999 A2 | 12/1985 | |
| WO | 2011/002278 A1 | 1/2011 | |
| WO | WO-2011002278 A1 * | 1/2011 | ............. A61K 8/817 |
| WO | 2011/103440 A1 | 8/2011 | |

OTHER PUBLICATIONS

Patarca et al.,Crit Rev Oncog. 2000;11(3-4):255-305.*
Steere,A.C. and Mallison,G.F. (1975) Handwashing practices for the prevention of nosocomial infections. Ann. Intern. Med., 83, 683-690.
Patarca,R., Rosenzwei,J.A., Zuniga,A.A., and Fletcher,M.A. (2000) Benzalkonium salts: Effects on G protein-mediated processes and surface membranes. Crit. Rev. Oncog., 11, 255-305.
Sep. 9, 2016—International Search Report and Written Opinion of PCT/NL2016/050326.
De Kraker,M.E., Davey,P.G., Grundmann.H.; Burden study group. (2011) Mortality and hospital stay associated with resistant *Staphylococcus aureus* and *Escherichia coli* bacteremia: Estimating the burden of antibiotic resistance in europe. PLoS Med., 8, e1001104.
Parvizi,J., Pawasarat,I.M., Azzam, K.A., Joshi,A., Hansen,E.N. and Bozic,K.J. (2010) Periprosthetic joint infection: The economic impact of methicillin-resistant infections. J. Arthroplasty, 25, 103-107.
De Kraker,M.E., Wolkewitz.M., Davey,P.G., Koller,W., Berger,J., Nagler.J., Icket,C., Kalenic,S. et al. (2011) Clinical impact of antimicrobial resistance in european hospitals: Excess mortality and length of hospital stay related to methicillin-resistant *Staphylococcus aureus* bloodstream infections. Antimicrob. Agents Chemother., 55, 1598-1605.
De Kraker,M.E., Wolkewitz.M., Davey,P.G., Koller,W., Berger,J., Nagler.J., Icket,C., Kalenic,S. et al. (2011) Burden of antimicrobial resistance in european hospitals: Excess mortality and length of hospital stay associated with bloodstream infections due to *Escherichia coli* resistant to third-generation cephalosporins. J. Antimicrob. Chemother., 66, 398-407.
Ciccolini,M., Donker.T., Grundmann,H., Bonten,M.J. and Woolhouse,M. (2014) Efficient surveillance for healthcare-associated infections spreading between hospitals. Proc. Natl. Acad. Sci. U. S. A., 111, 2271-2276.
Donker.T., Wallinga,J. and Grundmann.H. (2014) Dispersal of antibiotic-resistant high-risk clones by hospital networks: Changing the patient direction can make all the difference. J. Hosp. Infect., 86, 34-41.
Pittet.D., Allegranzi,B., Sax.H., Dharan.S., Pessoa-Silva,C.L., Donaldson,L. and Boyce,J.M. (2006) Evidence-based model for hand transmission during patient care and the role of improved practices. Lancet Infect. Dis., 6, 641-652.
Ciccolini,M, Donker.T , Köck.R., Mielke.M., Hendrix,R., Jurke,A., Rahamat-Langendoen,J., Becker,K., et al. (2013) Infection prevention in a connected world: The case fora regional approach. Int. J. Med. Microbiol., 303, 380-387.

(Continued)

*Primary Examiner* — Ali Soroush
*Assistant Examiner* — Courtney A Brown
(74) *Attorney, Agent, or Firm* — Banner & Witcoff, Ltd.

(57) ABSTRACT

The invention relates to the fields of microbiology and health care, in particular to means and methods for minimizing the spread of hospital-acquired (HA) infections e.g. between patients and healthcare workers. Provided is an antimicrobial composition comprising an antimicrobial agent, a pharmaceutically acceptable carrier material and a polymer, the polymer being an N-vinyl lactam copolymer, and the composition being capable of forming a slow release antimicrobial film when applied to a skin surface.

19 Claims, 9 Drawing Sheets

(56) References Cited

OTHER PUBLICATIONS

Figure 1:
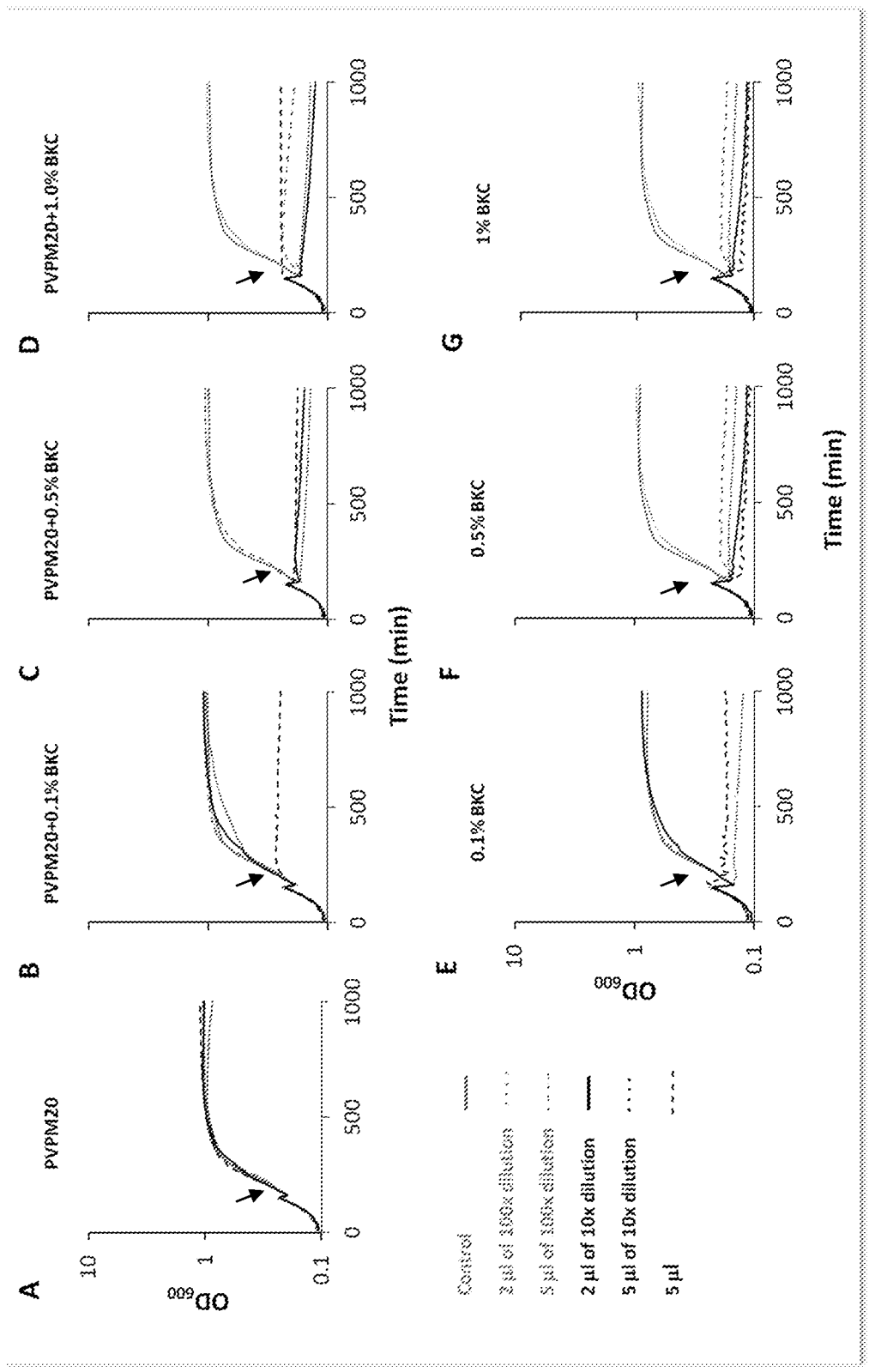

Curtis,V. and Carincross,S. (2003) Effect of washing hands with soap on diarrhoea risk in the community: A systematic review. Lancet Infect Dis, 3, 275-281.

Allegranzi,B. and Pittet,D. (2009) Role of hand hygiene in healthcare-associated infection prevention. J. Hosp. Infect., 73, 305-315.

Randle,J., Arthur,A. and Vaughan,N. (2010) Twenty-four-hour observational study of hospital hand hygiene compliance. J. Hosp. Infect., 76, 252-255.

Herbert,S., Ziebandt,A.K., Ohlsen,K., Schafer,T., Hecker,M., Albrecht,D., Novick,R. and Gotz,F. (2010) Repair of global regulators in *Staphylococcus aureus* 8325 and comparative analysis with other clinical isolates. Infect. Immun., 78, 2877-2889.

Kretzer,E.K. and Larson,E.L (1998) Behavioral interventions to improve infection control practices. Am. J. Infect. Control, 26, 245-253.

WHO. (2000) World health report 2000.

Basketter,D.A., Marriott,M., Gilmour,N.J. and White,I.R. (Apr. 2004) Strong irritants masquerading as skin allergens: The case of benzalkonium chloride. Contact Derm., 50, 213-217.

Larson,E. and Killien,M. (1982) Factors influencing handwashing behavior of patient care personnel. Am. J. Infect. Control, 10, 93-99.

Pittet,D. (2001) Compliance with hand disinfection and its impact on hospital-acquired infections. J. Hosp. Infect., 48, 40-46.

Yamamoto,K. (1995) Sensitive determination of quaternary ammonium salts by extraction-spectrophotometry of ion associates with bromophenol blue anion and coextraction. Anal. Chim. Acta., 302, 75-79.

\* cited by examiner

ANTIMICROBIAL COMPOSITIONS AND METHODS FOR REDUCING MICROBIAL CONTAMINATION

CROSS-REFERENCE TO RELATED APPLICATIONS

This application is a U.S. National Stage application under 35 U.S.C. § 371 of International Application PCT/NL2016/050326 (published as WO 2016/178578 A1), filed May 6, 2016 which claims the benefit of priority to European Application serial no. 15166652.6, filed May 6, 2015. Each of these prior applications is hereby incorporated by reference in its entirety.

The invention relates to the fields of microbiology and health care. In particular, it relates to means and methods for minimizing the spread of hospital-acquired (HA) infections e.g. between patients and healthcare workers.

The continuous threat of infections caused by a wide range of opportunistic microorganisms is one of the major concerns for hospitals and other healthcare institutions. Hospitalized patients are especially susceptible for infections due to their underlying illnesses that may render them frail and/or immunocompromised. Additionally, wounds resulting from trauma or surgical interventions represent a breach of the primary skin barrier through which pathogens can readily gain access to normally well-protected body sites. Today, the majority of the infections caused by bacteria can still be treated reasonably well with antibiotics. However, the growing incidence of infections with antibiotic resistant bacteria makes treatment increasingly difficult and very costly (1, 2). This is underpinned by recent studies showing that infections with multi-drug resistant bacteria, such as methicillin resistant *Staphylococcus aureus* (MRSA), lead to increased morbidity, mortality and length of stay in hospitals (3, 4). Especially HA bacterial infections are notorious for their drug resistant phenotypes, which originate from the continuously applied antibiotic pressure in nosocomial settings. Importantly, HA infections are to a large extent acquired and spread through direct contacts between patients and healthcare workers (5, 6, 7). Therefore, a major prerequisite for success in the fight against HA infections is the strict implementation of effective infection prevention measures (8).

One of the most effective precautions to minimize the spread of pathogens in healthcare settings is the routine decontamination of the hands of healthcare workers in-between patient contacts (7, 9). "Skin disinfectants" are routinely used in professional and non-professional contexts to rapidly kill microbes. A physician has a need to disinfect his or her skin both before and after examining a patient. Prior to the performance of an invasive medical procedure, the skin of the subject must be properly cleaned to avoid post-procedure infections. In non-professional contexts, a commuter, riding public transportation, may wish to disinfect her hands before handling food; a child, playing in a park, may need to clean his hands but not have the convenience of soap and water nearby. Each of these situations require, optimally, a skin disinfectant that is effective, easy to use, and non-irritating so as to permit repeated use.

On a worldwide scale, it has been estimated that the strict implementation of standard control measures, in particular hand hygiene, could save one million lives annually (10, 11). Importantly, the success of the implementation of such control measures relies strongly on the strict adherence of healthcare workers to the protocol for hand disinfection between patient contacts. Yet, it has been noted that many healthcare workers experience difficulties in complying strictly to hand disinfection protocols for a range of different reasons (12, 13, 14).

A key problem resides in the fact that effective hand hygiene requires the frequent re-application of soaps and alcohol- or chlorhexidine-based disinfectants. This can, on the long term, negatively affect the quality of the skin, resulting in skin irritation (15). In addition, skin damage due to the use of aggressive hand-washing products makes the skin more prone to colonization by pathogenic micro-organisms (16). Because chapped skin tends to be more susceptible to microbial contamination, repeated use of alcohol disinfectants can exacerbate the very problem they are intended to solve. Furthermore, whereas alcohol can be an effective disinfectant, once it evaporates its antimicrobial activity is lost.

To overcome at least some of the drawbacks of the repeated use of soaps or other disinfectants, the present inventors aimed at the development of a new antimicrobial composition for use as skin disinfectant and/or hand coating—herein also referred to as 'microglove'—with a protective (antibacterial) effect that would last in the minutes to hour time range. Ideally, the antimicrobial microglove should be in the form of a thin, comfortable polymer film that can be applied in the form of a hand rub, and that then covers the surface of the hands. Furthermore, to avoid interference with established hygiene regimens, the antimicrobial coating should be readily removable by hand washing with regular soap and water.

It was surprisingly observed that these goals could be met by the provision of an antimicrobial composition comprising an antimicrobial agent, a pharmaceutically acceptable carrier material and a novel polymer system, the composition being capable of forming a slow release antimicrobial film when applied to a skin surface. The composition according to the invention forms a protective film on the surface of the skin when applied, which film acts as a carrier from which the antimicrobial agent(s) is slowly released, thus providing prolonged hygiene.

The polymer system is an N-vinyl lactam copolymer of vinyl lactam monomers and hydrophobic maleate monomers derivatized with a pendant hydrophobic chain, like an aliphatic chain. It was observed that the film-forming and biocide release capacities of the copolymer are effected by the relative amount of the respective monomers within the copolymer. More in particular, it was surprisingly found that satisfactory results are obtained with a copolymer obtainable by solution polymerization, and wherein the monomers are fed continuously and simultaneously, as premixed monomer mixture comprising about 10-50 weight % of the hydrophobic maleate monomer, to the reaction mixture over a pre-determined period of time.

Accordingly, in one embodiment the invention provides an antimicrobial composition comprising an antimicrobial agent, a pharmaceutically acceptable carrier material and an N-vinyl lactam copolymer of the general Formula I Formula I

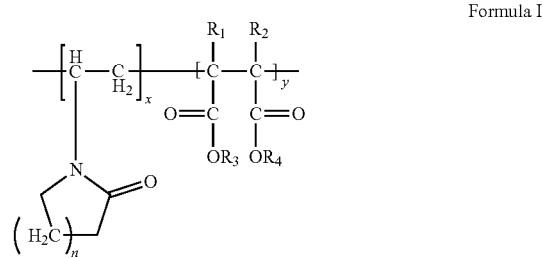

wherein n is 1 or 2; preferably n is 1
wherein 0.55≤x≤0.97 and y=1−x, preferably 0.65≤x≤0.97 and y=1−x, more preferably 0.88≤x≤0.97 and y=1−x;
$R_1$ and $R_2$ are each independently hydrogen or methyl, preferably wherein $R_1$ and $R_2$ are both hydrogen,
$R_3$ and $R_4$ are each independently selected from hydrogen, linear and branched alkyl or aralkyl groups, $R_3$ and $R_4$ comprising in total at least 2, preferably at least 4, more preferably at least 8 carbon atoms, with the exception that both $R_3$ and $R_4$ are hydrogen,
wherein said copolymer is preferably obtainable by solution polymerization of vinyl lactam monomer units (A) and derivatized maleate monomer units (B), wherein (A) and (B) are defined according to the following general formula:

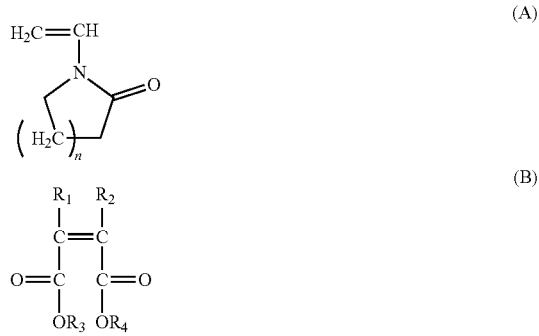

wherein said polymerization comprises the continuous feeding of a monomer mixture ("feed") comprising about 70-90 weight % of monomer (A) and 10-30 weight % of monomer (B), over a predetermined period of time to the reaction mixture. The composition is capable of forming a comfortable slow release antimicrobial film when applied to a skin surface.

The vinyl lactam monomer can comprise a 5-membered ring (pyrrolidone; n=1) or a 6-membered ring (caprolactam; n=2). Preferably, it is a vinyl pyrrolidone. In one embodiment, the polymer system comprises a PVP based co-polymer comprising derivatized (di) alkyl maleate as co-monomer units.

A composition of the invention is not disclosed or suggested in the art.

WO2012/146918 relates to a biocidal coating composition, particularly a hand sanitizer product, which exhibits long-term residual biocidal activity. Disclosed is a biocidal coating composition comprising a copolymer comprising vinylpyrrolidone monomer units and hydrophilic vinyl monomers comprising a hydrophilic moiety, such as (1-5C) alkyl substituted by a hydrophilic moiety. The only exemplified polymer is a terpolymer of (VP), dimethylaminopropyl methacrylamide (DMAPMA) and methacrlyoyaminopropyl lauryldimonium chloride (MAPL-DAC) (INCI name: Polyquaternium 55.) Nothing is mentioned about N-vinyl lactam copolymer of vinyl lactam monomers and hydrophobic maleate monomers, let alone alkyl-derivatized maleates.

WO2011/002278 relates to copolymers of vinyl lactams with derivatized maleates and their use in the area of personal and medical care and pharmaceuticals. Disclosed are copolymers of VP and maleates derivatized with one or two alkyl chains, wherein the alkyl is a linear or branched (hetero)alkyl chain, the alkyl chain comprising 1-99, preferably from 1-50 and more preferably from 1-30 carbon atoms. The exemplary co-polymers contain alkyl-maleates with up to eight C-atoms, and the weight ratio PV to alkyl-maleates used in the feed stream is up to about 60:40, thus resulting in a polymer containing a higher proportion of the hydrophobic maleates. More specifically, WO2011/002278 fails to teach a preference for N-vinyl lactam copolymers in combination with a biocide, wherein the vinyl lactam monomers and derivatized maleates are fed as premix in the relative weight ratio of 70-90% of monomer (A) and 10-30% of monomer (B) and wherein the maleate comprises one or two linear or branched alkyl(s).

Also known in the art is a complex called povidone-iodine formed by PVP added to iodine, that possesses disinfectant properties. The complex is used in various products like solutions, ointment, pessaries, liquid soaps and surgical scrubs. It is known under the trade names Betadine and Pyodine.

A copolymer for use in the present invention is essentially homogeneous in its composition in that the co-monomer sequence is randomly distributed over the polymer chains. The homogeneous copolymers of the invention are obtainable by solution polymerization of the vinyl lactam and derivatized maleate monomers in the presence of a free radical initiator. Preferred free radical initiators are either organic peroxides or azo initiators such as: t-butyl peroxide, lauroyl peroxide, decanoyl peroxide, t-butyl peroxypivalate, 2,2'-azodi(isobutyronitrile) and 2,2'-azodi(2-methylbutyronitrile), although other initiators known in the art may be used as well.

As is disclosed in WO2011/002278, such polymers are readily obtainable by the copolymerization of vinyl lactam monomers and derivatized maleate monomers, wherein the reaction is performed by solution polymerization, and wherein the monomers are fed continuously and simultaneously, e.g. as premixed monomer mixture, to the reaction mixture over a predetermined period of time. By controlling the amount, composition and mixture of derivatized maleates used during the polymerization with the vinyl lactam, a range of vinyl lactam based copolymers having a broad range of resultant solubilities and/or mechanical properties as well as low residual monomer levels can be efficiently synthesized.

More in particular, it was found in the present invention that a monomer mixture comprising about 70-90 weight % of vinyl lactam monomer (A) and 10-30 weight % of hydrophobically modified maleate monomer (B), yields a copolymer having unique film-forming and/or biocide release properties. The relative amounts of A and B monomers within the premixed feed can vary, depending on specific needs and/or chemical nature of the monomers. For example, the longer the pendant alkyl chain(s) of the B monomer, the less is needed to introduce sufficient hydrophobicity in the resulting N-vinyl lactam copolymer. Vice versa, B monomers with relatively short (e.g. up to 6 or 8 C-atoms) aliphatic chains, may be used at a higher weight percent. Likewise, the number of alkyl chains attached to the maleate can also be of influence. The skilled person will be able to optimize the reaction conditions for each specific situation using his common general knowledge.

In one aspect, the premixed monomer feed comprises about 75-85 weight % of vinyl lactam monomer (A) and about 15-25 weight % of monomer (B). In another aspect, the premixed monomer feed comprises about 80-90 weight % of vinyl lactam monomer (A) and about 10-20 weight % of monomer (B). Very good results can be obtained, e.g. when using monoalkyl or dialkyl maleates, comprising about 80 weight % of vinyl lactam monomer (A) and about 20 weight % of the (mono)alkyl maleate monomer (B).

Preferably, the mol % of the respective monomers in the feed are about 88-97 mol % of monomer (A) and 12-3 mol % monomer (B)

In a copolymer of the invention, $R_3$ and $R_4$ are each independently selected from hydrogen, linear and branched alkyl or aralkyl groups comprising at least 2 carbon atoms in total, with the exception that both $R_3$ and $R_4$ are hydrogen. The total number of C-atoms in the $R_3$ and $R_4$ moieties is at least 2, preferably at least 4, more preferably at least 6 or 8, such that sufficient hydrophobicity is introduced into the copolymer. In one aspect, the total number of C-atoms in the $R_3$ and $R_4$ moieties is up to 40, preferably up to 36. For example, it is in the range of 2-40; 8-36; 10-38, 12-34; 14-36 or 16-40.

In one aspect, $R_3$ and $R_4$ are each independently selected from hydrogen, linear and branched C1-C30 alkyl groups, and C1-C30 aralkyl groups, preferably hydrogen, linear and branched C4-C30 alkyl groups, and C4-C30 aralkyl groups. For example, each of $R_3$ and $R_4$ is independently selected from hydrogen, linear and branched C8-C26 alkyl groups, and C8-C26 aralkyl groups.

In a specific embodiment, $R_3$ and $R_4$ are each independently selected from hydrogen and linear and branched C14-C24 alkyl groups, preferably linear or branched C16-C22 alkyl groups.

The derivatized maleate can be symmetrical ($R_3$ and $R_4$ are the same) or asymmetrical ($R_3$ and $R_4$ are distinct). In one embodiment, $R_3$ and $R_4$ are identical alkyl or aralkyl groups. In another embodiment, $R_3$ and $R_4$ are different. For example, one of $R_3$ and $R_4$ is hydrogen and the other is alkyl or aralkyl. As another example, one of $R_3$ and $R_4$ is aralkyl and the other is alkyl. As yet another example, both of $R_3$ and $R_4$ are alkyl or aralkyl groups but each having a distinct structure, like a linear alkyl and a branched alkyl, or two alkyl groups having a different number of C-atoms.

In a specific aspect, at least one of $R_3$ and $R_4$ is a branched C20 or C22 alkyl chain. For example, the N-vinyl lactam copolymer is Poly[(vinyl pyrrolidone)-co-(octyl dodecyl maleate)]. In another specific aspect, at least one of $R_3$ and $R_4$ is a linear C8-C14 alkyl chain, preferably C10-C12 alkyl, more preferably C10 alkyl. For example, the maleate monomer is derivatized with one or two linear C8, C10, or C12 alkyl chains. In a preferred aspect, both $R_3$ and $R_4$ are linear C8-C14 alkyl, preferably C8-C10 alkyl or C10-C12 alkyl. Very good results are obtained using a di-C10 alkylated maleate. Preferably, the maleate monomer derivatized with one or two linear C8, C10, or C12 alkyl chains is used in the premixed monomer feed at about 10-20 weight % when preparing the copolymer.

Exemplary combinations of $R_3$ and $R_4$ in a derivatized hydrophobic maleate of the present invention are given in the following Table.

| R3 | R4 | R3 | R4 | R3 | R4 |
|---|---|---|---|---|---|
| C8-12 alkyl | C8-12 alkyl | C4 alkyl linear | C4 alkyl linear | C8-C12 alkyl linear | C2 alkyl linear |
| C14-28 alkyl | C8-12 alkyl | C2 alkyl linear | C6 alkyl linear | C20 alkyl branched | H |
| H | C8-12 alkyl | C2 alkyl linear | C8-12 alkyl linear | C12 alkyl linear | H |
| H | C14-28 alkyl | H | C20 alkyl branched | C20 alkyl branched | H |
| C16-C30 alkyl | C8-12 alkyl | H | C12 alkyl linear | C22 alkyl branched | H |
| C8-12 aralkyl | H | H | C20 alkyl branched | C30 alkyl branched | H |
| C12-C24 alkyl | C8-12 aralkyl | H | C22 alkyl branched | C30 alkyl linear | H |
| C18-30 aralkyl | C12-C24 alkyl | H | C30 alkyl branched | C20 alkyl branched | C20 alkyl branched |
| H | C12-C24 alkyl linear | H | C30 alkyl linear | C20 alkyl branched | C4 alkyl linear |
| C1-C6 alkyl | C1-C6 alkyl | C4-C10 alkyl | C1-C6 alkyl | C6-C20 alkyl | C1-C4 alkyl |
| H | C1-C6 alkyl | C4-C10 alkyl | C4-C10 alkyl | C3-C7 alkyl | C4-C10 alkyl |
| C10-C12 alkyl linear | C10-C12 alkyl linear | H | C10-C12 alkyl linear | C10-C12 alkyl linear | H |
| C16-C20 alkyl linear | H | C16-C20 alkyl linear | C16-C20 alkyl linear | H | C16-C20 alkyl linear |

Also provided is a method for providing an N-vinyl lactam copolymer of the general Formula I

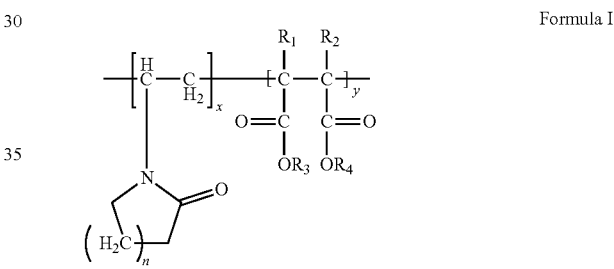

Formula I wherein n is 1 or 2; preferably wherein n is 1

$0.55 \leq x \leq 0.97$ and $y=1-x$, preferably $0.65 \leq x \leq 0.97$ and $y=1-x$, more preferably $0.88 \leq x \leq 0.97$ and $y=1-x$;

$R_1$ and $R_2$ are each independently hydrogen or methyl, preferably wherein $R_1$ and $R_2$ are both hydrogen, $R_3$ and $R_4$ are each independently selected from hydrogen, linear and branched alkyl or aralkyl groups, $R_3$ and $R_4$ comprising in total at least 2 C-atoms, preferably at least 4 C-atoms, with the exception that both $R_3$ and $R_4$ are hydrogen, comprising the solution polymerization of vinyl lactam monomer units (A) and hydrophobically derivatized maleate monomer units (B), wherein (A) and (B) are defined according to the following general formula:

(A)

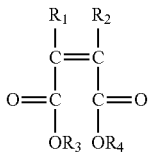
(B)

wherein said polymerization comprises the continuous feeding of a premixed monomer feed comprising about 70-90 weight % of monomer (A) and about 10-30 weight % of monomer (B), over a predetermined period of time to the reaction mixture.

As will be understood by a person skilled in the art, all preferences indicated herein above and below for the polymer and/or monomers (R-groups; monomer mixing ratio's, etc.) are also applicable to the method for preparing the polymer.

The monomers are suitably pre-mixed in a suitable solvent and fed over a predetermined time into a pre-heated reaction vessel containing the same solvent as used to dilute the monomer mix. Any solvent or solvent mixture may be used in which the monomers and, optionally also the resulting copolymer, are freely soluble. Suitable solvents include alcohols, esters and alkanes. For instance, ethanol, isopropanol, ethyl acetate, isopropyl acetate, propane diol, or any mixture thereof, is used. If the (di)alkyl maleate is considerably hydrophobic in nature, pentane, hexane or heptanes may be used, for instance. When desired, the polymerization can be conducted directly in a preferred skin care oil, skin care solvent, skin care emulsifier or skin care emollient of natural or synthetic origin. Examples include skin care oils, solvents or emollients selected from the group consisting of natural vegetable oils, natural nut and seed oils, natural based and/or synthetic emulsifiers, natural based and/or synthetic emollients, in particular ester based emollients.

The reaction set-up, monomers, solvent and initiator are typically inerted prior to the start of the polymerization with a gas, such as nitrogen or argon. It is preferred to add the initiator in a continuous fashion in order to best keep the monomer/initiator constant over time. However, the initiator can be added at the start of the reaction and/or during the reaction at multiple fixed amounts if continuous feeding proves too difficult.

The monomers are fed continuously as a preformed monomer mixture to the reaction kettle over a predetermined period of time. This ensures that that the desired monomer ratio is held constant over time resulting in a synthesized polymer having the same general compositional make-up. Because the association of vinyl lactam with maleate in solution results in the "activation" of the maleate and increases its reactivity to undergo efficient polymerization, it is important to introduce the monomers in such a way that both species are present during the polymerization process and at the defined weight ratio of vinyl lactam to maleate.

The monomers should be introduced in the reactor in such a way to maximize the association and subsequent maleate activation. It is desirable to add the monomers in a continuous fashion in order to ensure that the monomers are present in the proper concentrations throughout the polymer process and ensure no reacting species are being depleted in an undesirable fashion. Furthermore, the monomer feed time may be selected to provide a desired high copolymer solids level, suitably at least 30 minutes, and generally 1 to 5 hours, depending upon the predetermined feed rate.

Following completion of the addition of the reaction mixture, the reaction is generally allowed to proceed for a period of several additional hours. The total reaction time typically ranges from about 1 hour to about 48 hours, more preferably from about 5 to about 15 hours.

The polymerization reaction is carried out at a suitable temperature, generally about 50-150° C., preferably 60-100° C. The exact reaction temperature is generally decided by the decomposition rate of the initiator system being used. Generally, reaction temperatures are employed in which the initiator's decomposition half-life is between about 15 minutes and about 5 hours, more preferably between about 1 hour and about 3 hours. Either single initiator or multi initiator systems can be employed in the reaction. Multi-initiator systems are often advantageous because one initiator is used to react the bulk of the monomer(s) while a higher decomposing temperature initiator is used to react the residual monomer at higher temperatures. In a specific embodiment, a first portion of a monomer mixture in a suitable solvent is heated to a temperature of about 75° C., followed by the continuous yet separate addition of a polymerization initiator and a second portion of the monomer mixture during a predetermined time period, e.g. 1-4 hours. Then, the reaction is allowed to proceed for a further 1-30 hours, preferably 2-10 hours at the same temperature. Then, the temperature may be raised, e.g. to about 80-85° C., and the reactants are allowed to react further under slight reflux for some hours, typically 1-4 hours to react any residual monomer. It can be advantageous to add additional initiator charges to the reaction during this period in order to ensure there is initiator available for the continuous reacting of monomer. Thereafter, the polymer solution thus obtained may be cooled and discharged. Good results are obtained when the polymerization reaction is conducted at a solids level of between about 10% and 70% solids, preferably 20% to 50%.

The polymerization procedure may of course comprise one or more additional steps if desired. In one embodiment, it further comprises the step of exchanging the solvent or solvent mixture used during solution polymerization for a biocompatible solvent. Alternatively, or additionally, the copolymer can be isolated via solvent drying. Both the solvent exchange and solvent drying techniques are known in the art. Another alternative is precipitating the copolymer from the reaction mixture into a proper non-solvent, or adding a proper non-solvent to the reaction mixture. Precipitation may be repeated to further lower the impurity level of the copolymer when desired. Also, wash/extraction steps may be applied to the isolated copolymer for reducing the presence of any impurities. In one embodiment, the polymerization solvent is chosen such that the copolymer formed precipitates from the reaction mixture once the critical molecular weight has been reached.

The resulting N-vinyl lactam copolymer may suitably be present in the antimicrobial composition at a concentration of about 0.05-10 weight percent, preferably 0.1-8 weight percent, more preferably about 0.5-6 weight percent.

The antimicrobial composition may comprise between about 0.01 and 10 weight percent antimicrobial agent; preferably at a concentration between 0.05 and 2 weight percent, more preferably between 0.1 and 1 weight percent. Suitably the weight ratio of the N-vinyl lactam copolymer to antimicrobial agent is from 100:1 to 1:1, suitably from 50:1 to 1.5:1, suitably 20:1 to 2:1. Suitably the amount of antimicrobial agent is calculated as the sum of all antimicrobial agents.

In a particular embodiment, the antimicrobial composition comprises:
0.05% to 5% w/w of the antimicrobial agent
0.01% to 10% w/w of the N-vinyl lactam/maleate copolymer(s);
15 to 99.9% w/w of the carrier material.

The antimicrobial agent is advantageously is selected from the group consisting of quaternium salts, phenols, halogen-releasing compounds, aldehydes, biguanides and polymeric biguanides, amphoterics, iodine-based compounds, peroxygen-based compounds, and silver-containing compounds, and mixtures thereof. For example, in one preferred embodiment poly(hexamethylenebiguanide hydrochloride); PHMBH+Cl—) is used as antimicrobial agent.

In another preferred aspect, the antimicrobial agent is a quaternary ammonium compound, preferably selected from the group consisting of benzethonium chloride, other benzalkonium or benzethonium halides, including, benzalkonium or benzethonium bromide, chloride or fluoride, cetyl pyridinium chloride, dequalinium chloride, N-myristyl-N-methyl-morpholinium methyl sulfate, poly[N-[3-(dimethylammonio)propyl]-N'-[3-(ethyleneoxyethelene dimethylammoinio)propyl]urea dichloride], alpha-4-[1-tris(2-hydroxyethyl)ammonium chloride-2-butenyl]-omega-tris(2-hydroxyethyl)ammonium chloride, poly[oxyethylene (dimethyliminio)ethylene (dimethyliminio)-ethylene dichloride]. In a specific embodiment, the composition comprises benzalkonium chloride (BKC) or benzethonium chloride (BEZ). For example, the antimicrobial composition may comprise:
0.05% to 5% w/w of benzalkonium chloride or benzethonium chloride
0.01% to 10% w/w of N-vinyl lactam/maleate copolymer;
20 to 99.9% w/w of alcohol.

Phenols (phenol derivatives) which may be used according to the invention include, but are not limited to, 2-hydroxyphenol compounds such as triclosan (2,4,4'-trichloro-2'-hydroxydiphenyl ether, also available as IRGASAN DP300 from Ciba Specialty Chemicals Corp, Greensboro, N.C.) and 2,2'-dihydroxy-5,5'-dibromo-diphenyl ether; p-nitrophenol, picric acid, xylenol, phenoxyethanol, chlorinated phenols such as parachlorometaxylenol, p-chloro-o-benzylphenol and -dichlorophenol, cresols such as p-chloro-m-cresol, pyrocatechol, resorcinol, 4-n-hexylresorcinol, pryogallol, phloroglucin, carvacrol, thymol, p-chlorothymol, o-phenylphenol, o-benzylphenol, phenol, 4-ethylphenol, 4-phenolsulfonic acids, hexachlorophene, tetrachlorophene, dichlorophene, 2,3-dihydroxy-5,5'-dichlorophenyl sulfide, 2,2'-dihydroxy-3,3',5,5'-tetrachlorodiphenyl sulfide, 2,2'-dihydroxy-3,3',5,5',6,6'-hexachlorodiphenyl sulfide and 3,3'-dibromo-5,5'-dichloro-2,2'-dihydroxydiphenylamine. Preferred is triclosan at a concentration of between about 0.1 and 2 percent and most preferably between about 0.3 and 1 percent. Other phenols may be comprised at concentrations of between about 0.3 and 2 percent, but preferably at concentrations equivalent in potency against S. aureus as between 0.3 and 1 percent triclosan.

Additional antimicrobial agents which may be incorporated into compositions of the invention include antifungal agents such as miconazole (preferably at a concentration of 1-2 percent), polymixin (preferably at a concentration of 0.3-1 percent), neomycin (preferably at a concentration of 0.1-0.5 percent), iodine compounds such as povidone iodine (preferably at a concentration of 1-10 percent), minocycline (preferably at a concentration of 0.3-1.0 percent), and metal salts such as silver sulfadiazine (preferably at a concentration of 1-2 percent).

The antimicrobial composition may suitably comprise 15 to 99.9% w/w of a pharmaceutically acceptable carrier material, suitably at least 80% w/w, suitably at least 85% w/w, suitably at least 90% w/w. For example, the pharmaceutically acceptable carrier material may be a diluent, like an alcohol, water, an ester, a skin care oil, an emulsifier or emollient. Water used in the formulations is preferably deionized water having a neutral pH. Suitable alcohols include aliphatic alcohols. Preferably, the carrier material is selected from ethanol, isopropyl alcohol, propyl alcohol, and any mixture thereof.

An emollient, which may be, for example, an organic, a hydrocarbon-based or a fatty-ester based emollient. Suitable hydrocarbon-based emollients include petrolatum and mineral oils. Suitable fatty ester based emollients include methyl, isopropyl and butyl esters of fatty acids such as isopropyl palmitate, isopropyl myristate, isopropyl isostearate, isostearyl isostearate, diisopropyl sebacate, and propylene dipelargonate, 2-ethylhexyl isononoate, 2-ethylhexyl stearate, $C_{12}$-$C_{16}$ fatty alcohol lactates such as cetyl lactate and lauryl lactate, isopropyl lanolate, 2-ethylhexyl salicylate, cetyl myristate, oleyl myristate, oleyl stearate, oleyl oleate, hexyl laurate, and isohexyl laurate. Additional useful emollients include lanolin, olive oil, cocoa butter, and shea butter.

As will be understood by the person skilled in the art, the composition may further comprise pharmaceutically acceptable excipients selected from one or more of thickening agents, emulsifying agents, preservatives, chelating agents, pH modifiers, coloring agents, perfumes, and antioxidants.

Surfactants and/or emulsifiers (collectively referred to hereinafter as emulsifiers), preferably include non-ionic or cationic self-emulsifying waxes that are preferably soluble in alcohol at ambient temperature including Incroquat Behenyl TMS, Incroquat Behenyl TMS-50, Polawax, stearyl alcohol and cetearyl alcohol. These emulsifiers are present at a concentration between 0.05 and 3.0 percent. Emulsifiers preferably include Incroquat Behenyl TMS, which is a mild cationic emulsifier as well as an excellent conditioner, and Polawax, which is a non-ionic self emulsifying wax, individually at a concentration of between 0.05 and 0.5 percent, and in combination at a concentration of between 0.05 and 0.5 percent, more preferably in combination at a concentration ratio of approximately 1:1. If more than one emulsifier is used, it is preferred that the total concentration of all of the emulsifier is between 0.05 and 0.5 percent of the total concentration.

The invention also provides a method for reducing or eliminating the number of micro-organisms on a surface, comprising applying an antimicrobial composition according to the invention to said surface and allowing the formation of an antimicrobial film. The antimicrobial composition of the invention is advantageously used in a method for reducing or eliminating the number of bacteria, viruses, fungi and/or yeast on a surface. In one aspect the composition has activity against bacteria, including *Staphylococcus aureus, Pseudomonas aeruginosa, Enterococcus hirae, Escherichia coli, Salmonella, Acinetobacter, Proteus mirabilis* etc. Typically, the amount of composition applied is sufficient to maintain said reduction or elimination during at least 20 minutes, preferably at least one hour, more preferably several hours.

In one embodiment, the surface is the surface of a human body or part thereof, preferably skin, hair and/or nails. In another embodiment, the surface is the surface of an object, like a medical device or a personal care product.

Also provided is a coated substrate, comprising a substrate surface that is coated with an antimicrobial composition according to the invention; wherein the biocidal coating comprises a biocide and a polymer which comprises vinyl lactam monomer units and hydrophobically derivatized maleate monomer units. In one embodiment, the coated substrate is a human hand. Hence, the invention also provides the use of an antimicrobial composition according to the invention as skin sanitizer, hand-rub or "invisible" (micro)glove.

Furthermore, the antimicrobial skin sanitizing compositions of the present disclosure may be incorporated into or onto a substrate, such as a wipe substrate, an absorbent substrate, a fabric or cloth substrate, or a tissue substrate, among others. For example, the compositions may be incorporated into personal care products, such as wipes, absorbent articles, bath tissues, cloths, and the like. More particularly, the antimicrobial composition may be incorporated into wipes such as wet wipes, hand wipes, face wipes, cosmetic wipes, and the like, or absorbent articles, such as diapers, training pants, adult incontinence products, feminine hygiene products, and the like, and combinations thereof. In one preferred embodiment, the antimicrobial skin sanitizing composition is a liquid composition that may be used in combination with a wipe substrate to form a wet wipe or may be a wetting composition for use in combination with a dispersible wet wipe. In another embodiment, the antimicrobial skin sanitizing composition can be used in combination with a wipe substrate, which is packaged together with one or more absorbent articles, such as diapers.

Still a further aspect relates to the use of a co-polymer of a vinyl lactam monomer (A) and a hydrophobically derivatized maleate monomer (B), preferably alkyl maleate and/or dialkyl maleate, as slow-release carrier for an antimicrobial agent in an antimicrobial film or coating. As explained herein above, the copolymer is preferably obtainable by a process involving the continuous feeding of a premixed monomer mixture comprising a specific weight ratio of the distinct monomers.

LEGEND TO THE FIGURES

FIG. 1. Growth of S. aureus HG001 in polymer-coated microtiter plates. Different amounts of serially diluted PVPM20-90:10 formulations and unaided benzalkonium chloride (BKC) solutions were used to coat wells in a 96-well microtiter plate. These PVPM20-90:10 formulations and unaided BKC solutions contained increasing BKC concentrations as indicated. S. aureus HG001 was precultured in TSB using uncoated 96-well microtiter plates until early exponential growth after which aliquots of 100 µl were transferred to the polymer-coated wells (indicated by the arrows). Subsequently, growth at 37° C. for 1000 min was monitored by optical density readings at 600 nm.

Figure 2:
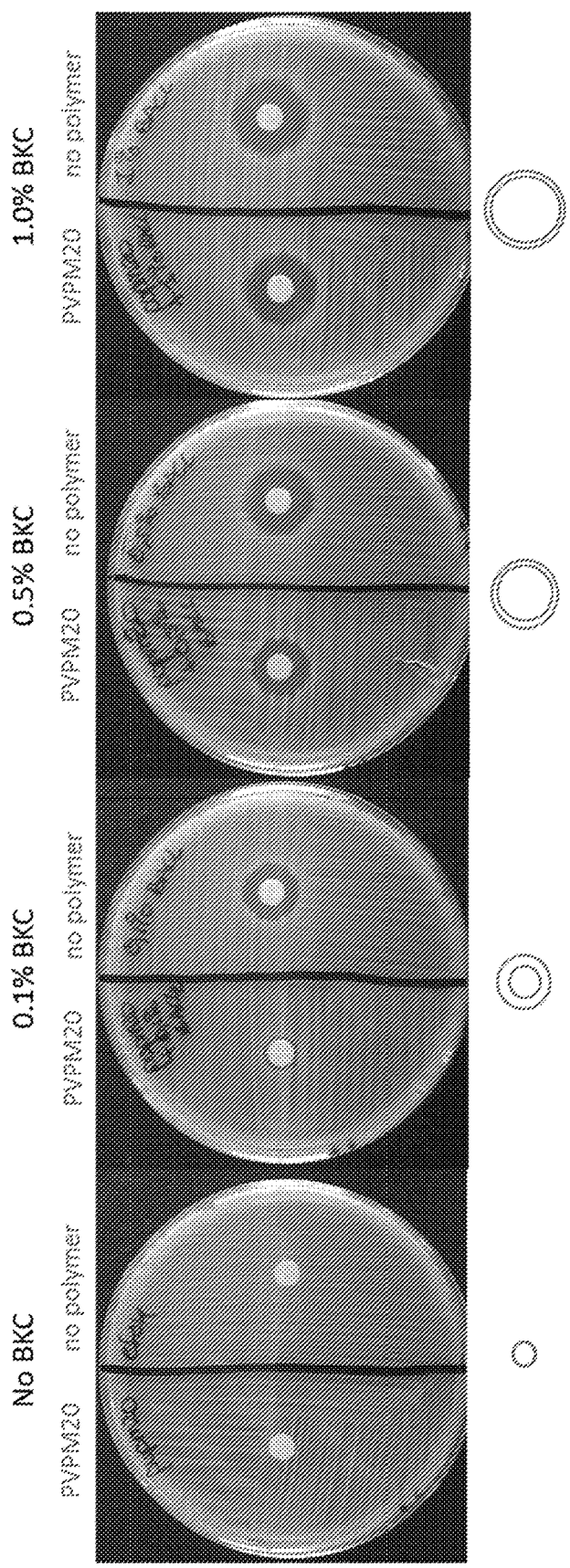

FIG. 2. BKC disk diffusion assay in the presence or absence of PVPM20-90:10. TSA plates were inoculated confluently with S. aureus HG001. Next, Whatman paper disks loaded with BKC at different concentrations (0.1%, 0.5% or 1%) either with or without PVPM20-90:10 were placed on top of the plates. After overnight incubation at 37° C. growth inhibition zones were detectable around the paper disks. The circles underneath the images of the plates represent the respective sizes of the inhibition zones when disks were loaded with BKC alone or with BKC plus PVPM20-90:10; the circle underneath the first plate (no BKC) indicates the size of the paper disk.

Figure 3:
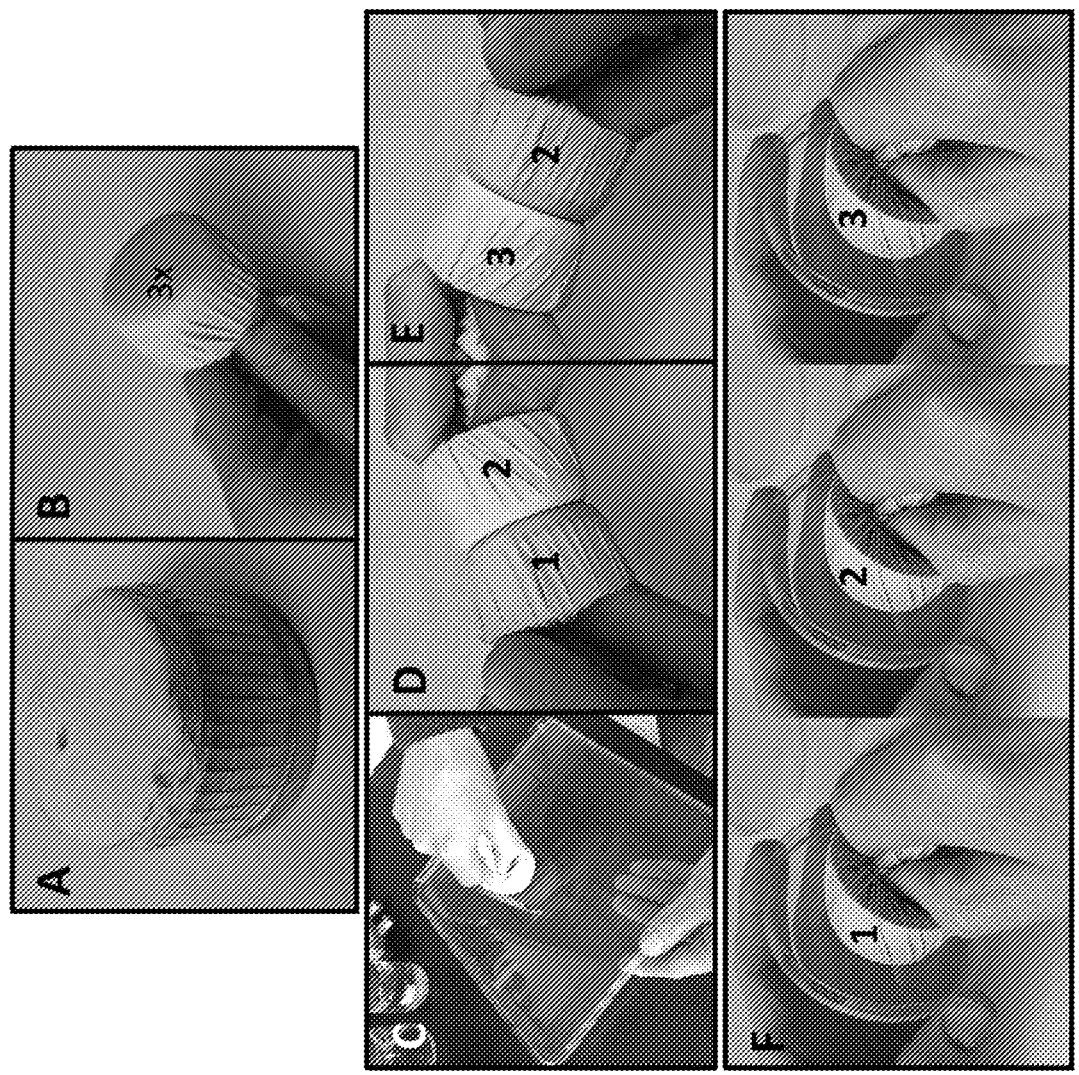

FIG. 3. Design of a contamination and transmission assay. (panel A) Stamp design; stamps were made of screw caps for laboratory flasks on top of which absorption paper was fixed with parafilm. (panel B) Example of one of the three stamps wrapped with a nitrile examination glove. (panel C) Contamination procedure; a first stamp (no. 1) was pressed for 10 sec onto a TSA plate inoculated with S. aureus HG001. (panel D) First transmission step; stamp no. 1 was pressed to stamp no. 2 for 5 sec. (panel E) Second transmission step; stamp no. 2 was pressed to stamp no. 3 for 5 sec. (panel F) Contamination of stamps with S. aureus HG001 was assessed by pressing the stamps onto TSA plates.

Figure 4:
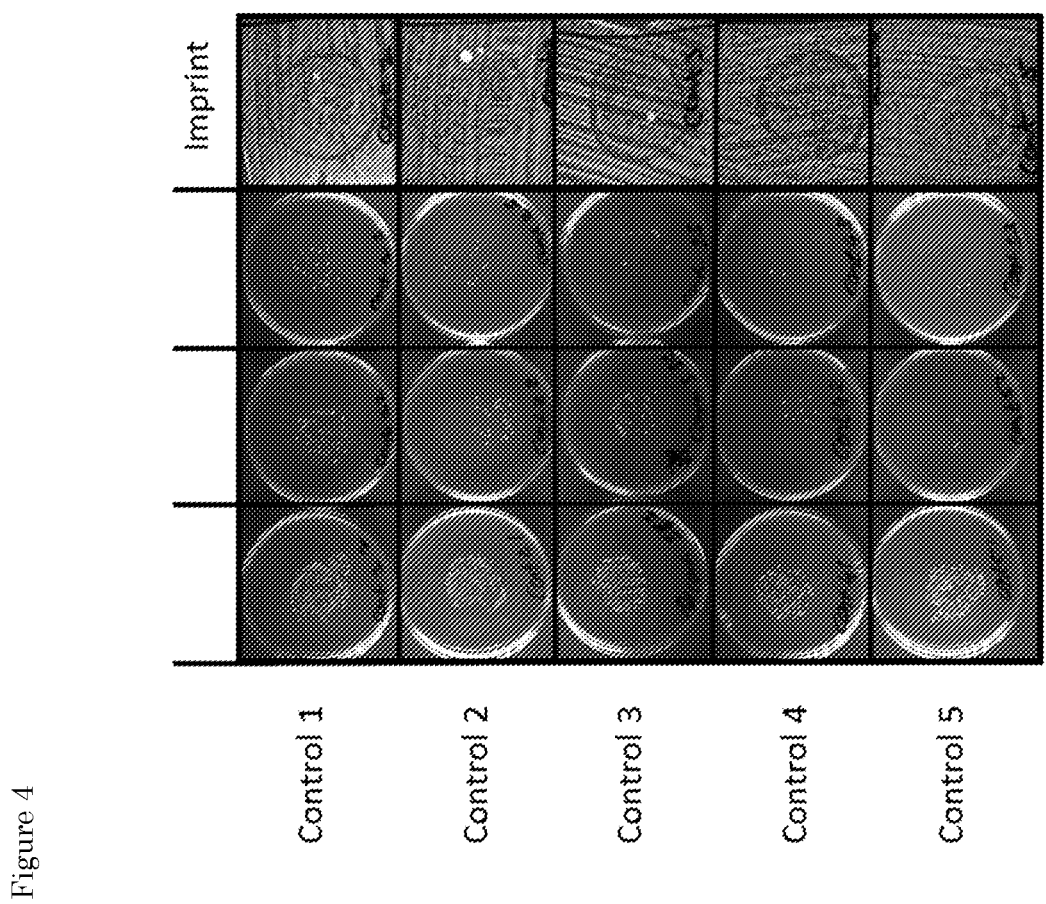

FIG. 4. Controls for the contamination and transmission assay. The first three columns depict the contamination of the three stamps with S. aureus HG001 as reflected by colony formation on the fresh TSA plates onto which the non-polymer-coated stamps were pressed. The last column shows the imprint that was left on the 'contamination plate' (inoculated with S. aureus HG001) after overnight incubation.

Figure 5:
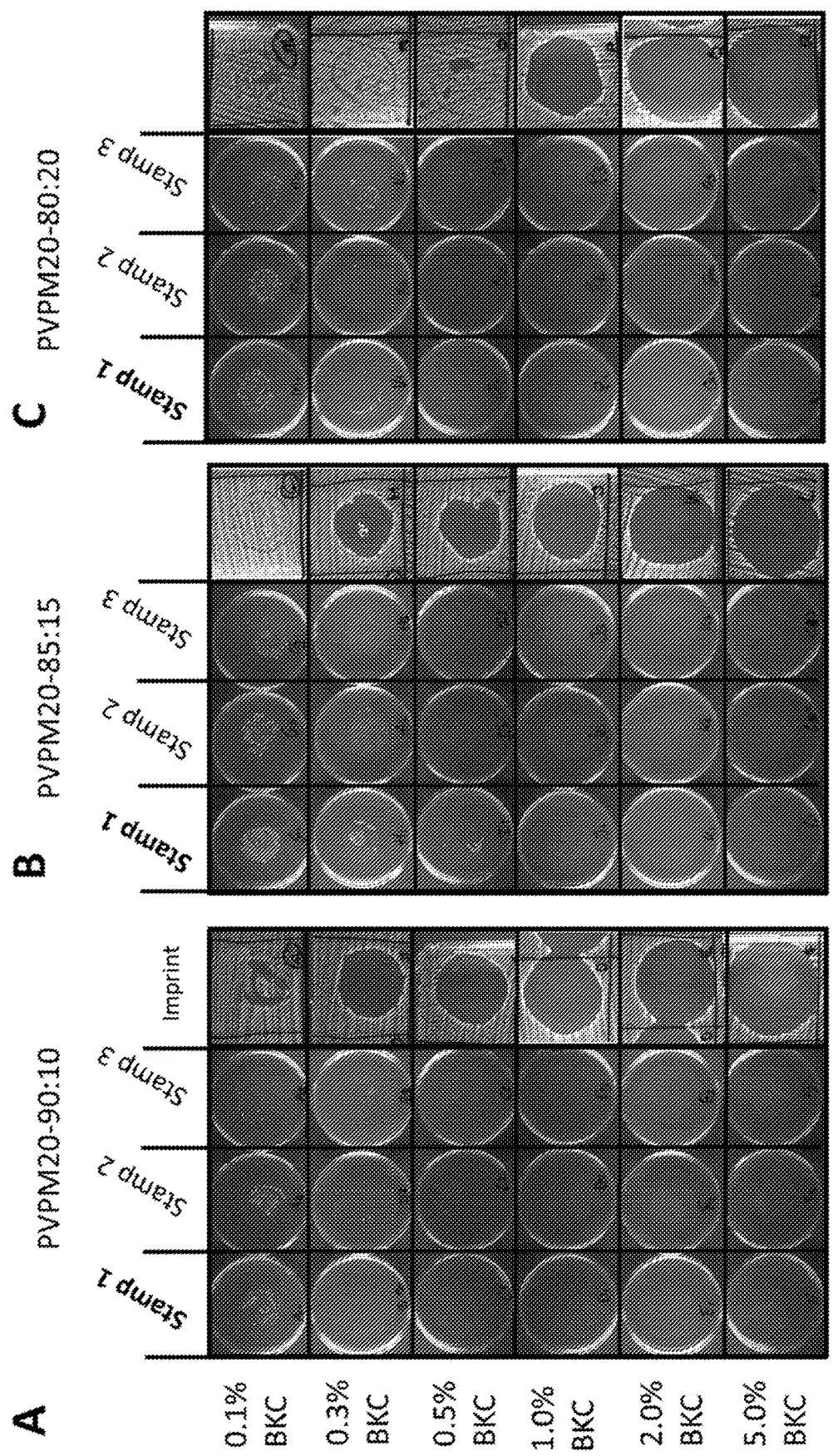

FIG. 5. Effects of polymer coating on contamination and transmission. Stamps were coated with (A) PVPM20-90:10, (B) PVPM20-85:15, or (C) PVPM20-80:20 supplemented with different concentrations of BKC as indicated. The first 3 columns depict the contamination of the three stamps with S. aureus HG001 as reflected by colony formation on the fresh TSA plates onto which the stamps were pressed. The last column shows the imprint that was left on the contamination plate (inoculated with S. aureus HG001) after overnight incubation.

FIG. 6.

Growth inhibition zones on TSA-plates with S. aureus HG001 after incubation at 37° C. The first well of a 96-well plate was coated with 20 µl formulations based on PVPDDM-80:20 2.5 wt % and 0.45 wt % biocide in alcohol. After drying, 100 µl water was added to the coated well and the plate was incubated for 60 seconds. Next, the aqueous phase was removed from the well. This process was repeated 7 times. Five µl aqueous phase of each incubation step was brought on the plate.

Formulations supplemented with BKC (A), BEZ (B), or PHMBH+Cl—) (C) showed growth inhibition up to the $4^{th}$, $4^{th}$ and $3^{rd}$ incubation, respectively.

Figure 7A:
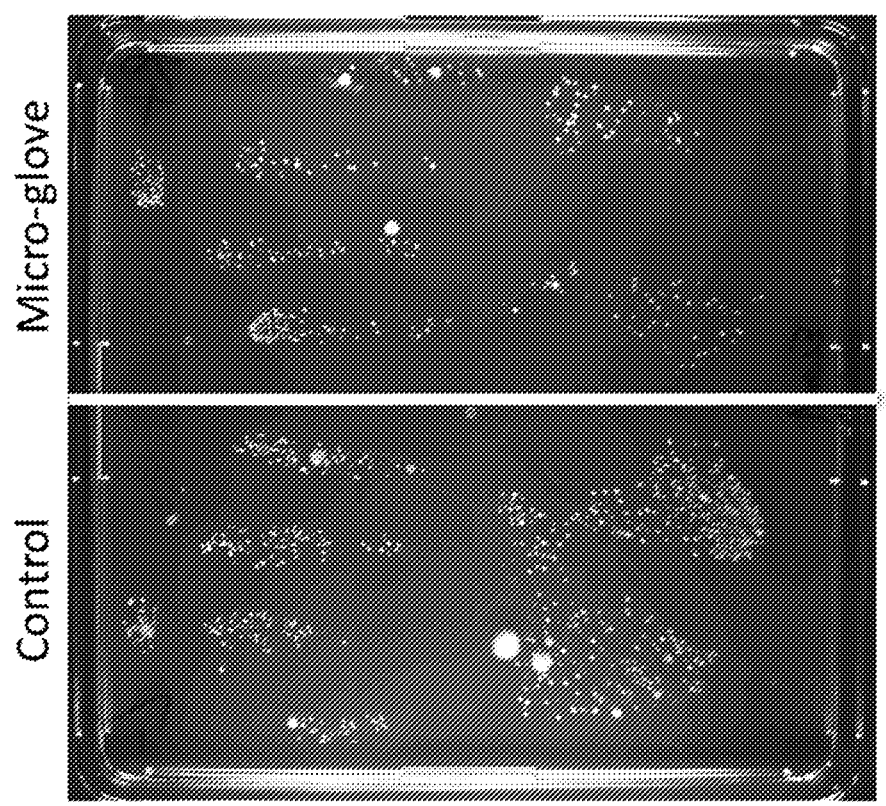
Figure 7:
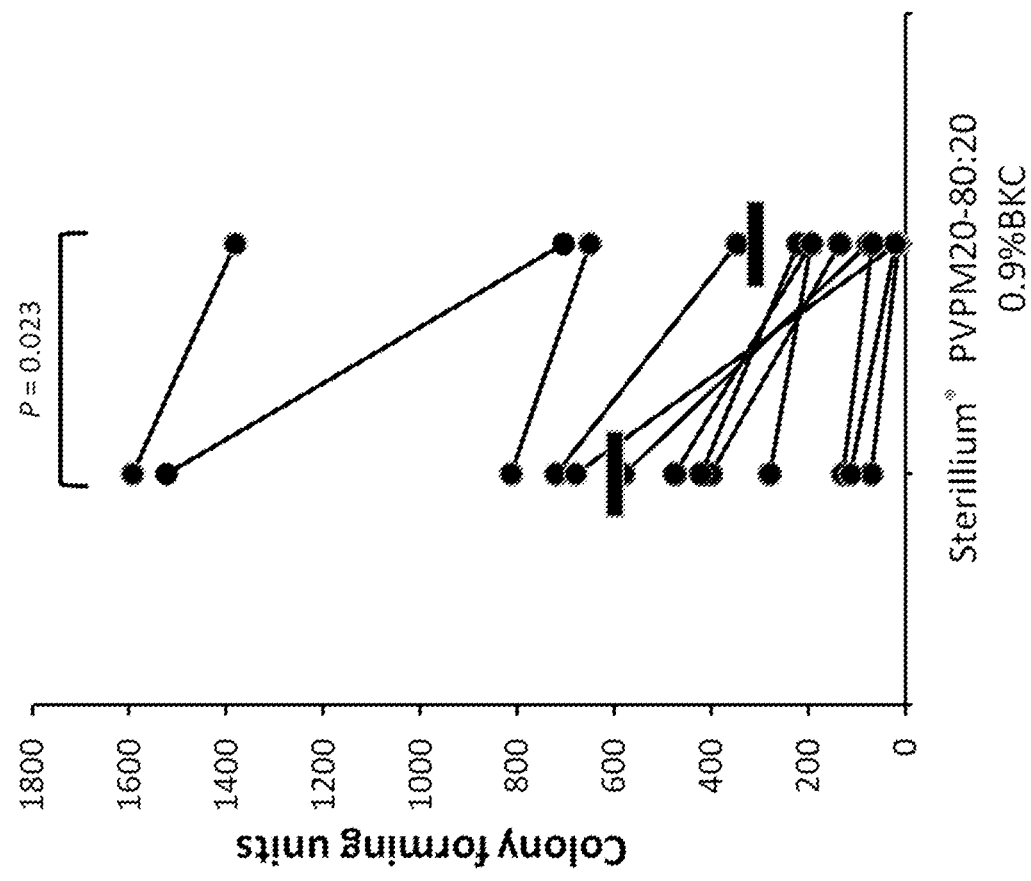

FIG. 7. Effects of polymer coating on microbial glove contamination. (panel A) Exemplary plate depicting the contamination of polymer-coated and non-coated examination gloves. The gloves were worn by a volunteer for 3 hours during which time the volunteer performed regular activities. Subsequently, the volunteer gently pressed the gloves onto a bioassay plate with LB agar. The picture was taken with the Syngene G:BOX after overnight incubation at 37° C. In this example, the left glove was used as an uncoated control, while the right glove was coated with PVPM20-80:20 0.9% BKC. (panel B) Results of the glove contamination assays. Coated and non-coated gloves were worn by 13 volunteers for about 3 hours. Colony forming units on the LB plates onto which the used gloves were pressed, were counted with the Syngene software. The diagram shows the comparison of the contamination of each pair of coated and non-coated gloves for each individual. Statistical analyses were done using the Mann-Whitney U test. Horizontal black bars indicate average numbers of colony forming units.

Figure 8:
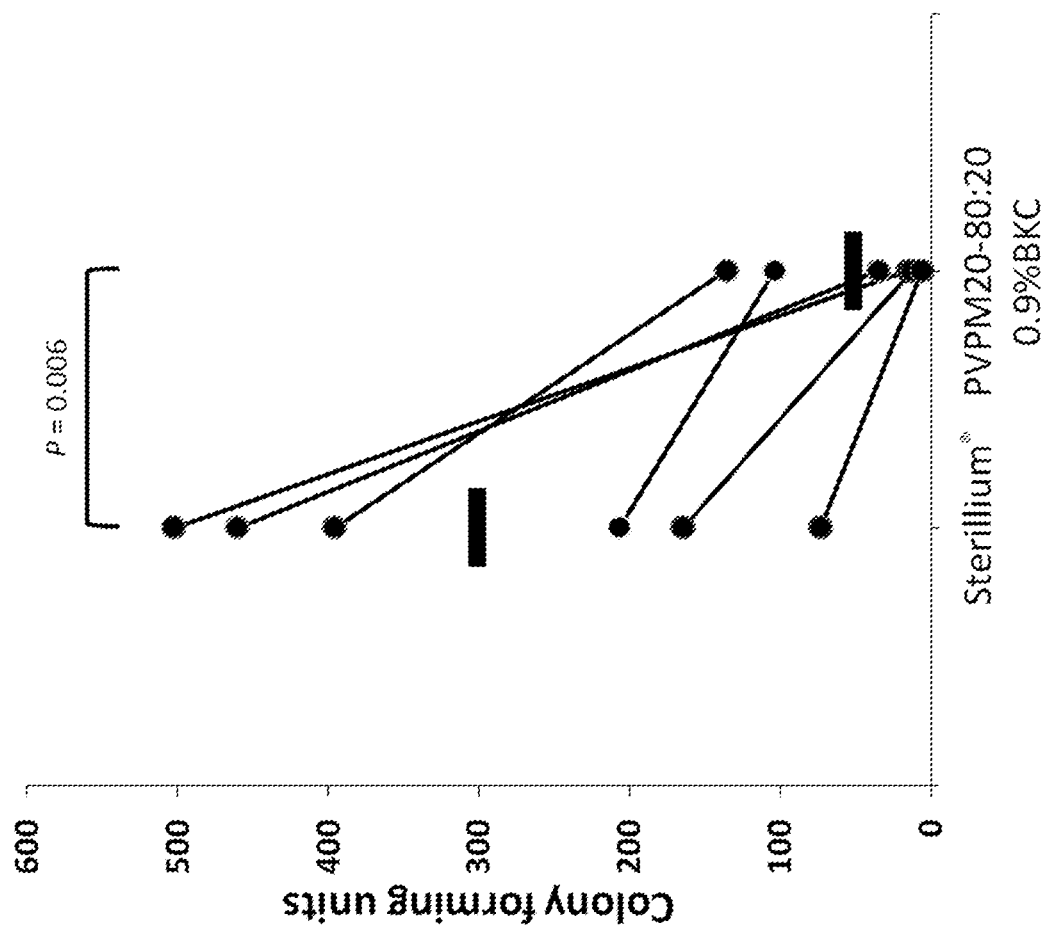

FIG. 8. Effects of polymer coating on microbial hand contamination. One hand of three volunteers was coated with PVPM20—80:20 0.9% BKC, while the other hand of these volunteers was left untreated. After 3 hours of regular activity, the volunteers pressed their hands gently onto LB bioassay plates. The plates were then incubated overnight at 37° C. Next day, images of the plates were recorded with the Syngene G:BOX, and colony forming units where assigned with the Syngene software. All individual experiments, including repeats, are indicated the diagram and allow the comparison of the contamination of each pair of polymer-coated and non-coated hands. Statistical analyses were done using the Mann-Whitney U test. Horizontal black bars indicate average numbers of colony forming units.

EXPERIMENTAL SECTION

Materials and Methods
Strains and Growth Media

S. aureus HG001 (21) was grown in TSB or on TSA. Liquid S. aureus HG001 cultures were grown in 96-well plates at 37° C. and under constant agitation using a Biotek powerwave microplate reader.

Monomer and Co-Polymer Synthesis
Monomer Synthesis: Octyl Dodecyl Maleate (M20).

Maleic anhydride (94.70 g, 1.01 mol) and 2-octyl-1-dodecanol (300.51 g, 1.00 mol) were stirred in a molten state at 50° C. for 24 hours. Hexane (600 ml) was added to the homogenous reaction mixture and stirred for 1 h at 60° C. The solution was left overnight at 4° C. and filtered over a Büchner funnel. A bright white powder of M20 (290.10 g, 73%) was obtained.

Monomer Synthesis: Mono-Decyl Maleate (MDM).

Maleic anhydride (49.52 g, 0.505 mol) and 1-decanol (79.14 g, 0.500 mol) were stirred in a molten state at 60° C. for 24 hours. Heptane (300 ml) was added to the homogenous reaction mixture and stirred for 1 h at 60° C. The solution was left overnight at 4° C. and filtered over a Büchner funnel. A bright white powder of MDM (96.13 g, 75.0%) was obtained.

Monomer Synthesis: Di-Decyl Maleate (DDM).

Maleic anhydride (32.65 g, 0.333 mol) and 1-decanol (110.80 g, 0.700 mol) were stirred in a molten state at 70° C. for 240 hours. The resulting mixture of mono- and di-substituted molecules was separated using ethyl acetate and bicarbonate solution. The DDM was further purified by vacuum distillation at 90° C. A clear, slightly yellow liquid of DDM (45.70 g, 33.1%) was obtained.

Monomer Synthesis: Mono-Eicosanoyl Maleate (MEM).

Maleic anhydride (25.14 g, 0.255 mol) and 1-eicosanol (74.64 g, 0.250 mol) were stirred in a molten state at 90° C. for 24 hours. Heptane (300 ml) was added to the homogenous reaction mixture and stirred for 1 h at 90° C. The solution was left overnight at 4° C. and filtered over a Büchner funnel. A bright white powder of MEM (83.29 g, 83.9%) was obtained.

The table below gives an overview of the copolymers used in the examples:

| Copolymer | R3 or R4 | R3 or R4 |
|---|---|---|
| PVPM20-65:35 | H | Branched C20 |
| PVPM20-80:20 | H | Branched C20 |
| PVPM20-85:15 | H | Branched C20 |
| PVPM20-90:10 | H | Branched C20 |
| PVPMDM-60:40 | H | Linear C10 |
| PVPMDM-75:25 | H | Linear C10 |
| PVPMEM-70:30 | H | Linear C20 |
| PVPDDM-80:20 | Linear C10 | Linear C10 |

Poly[(vinyl pyrrolidone)-co-(octyl dodecyl maleate)] (PVPM20 80/20)

N-vinyl pyrrolidone (40.63 g, 365.57 mmol) and octyl-dodecyl maleate (10.02 g, 25.30 mmol) were mixed together to give a clear solution at room temperature (monomer mixture). 0.20 g lauroyl peroxide was added to a 500 ml 3-neck round bottom flask fitted with a mechanical stirrer, a dropping funnel and 200 ml heptane. The monomer mixture was added to the dropping funnel. The entire set-up and reactants were inerted with argon gas and the temperature raised to 70° C. Upon reaching 70° C., the monomer mixture was added over a period of 2 hours. Subsequently 0.1 g lauroyl peroxide was added and the mixture was stirred at 70° C. for another 2 hours. During reaction the polymer precipitated from the solution. The formed polymer was washed three times with water and once with acetone. The collected polymer was dried overnight in an oven at 60° C. White powder of poly[(vinyl pyrrolidone)-co-(octyl dodecyl maleate)] 80/20 (64%) was obtained. The molecular weight of the polymer, determined with GPC using PEG standards, was Mn 23,918 and Mw 35,654. Poly[(vinyl pyrrolidone)-co-(octyl dodecyl maleate)]. The 90/10, 85/10 and 65/35 copolymers were prepared a similar way.

Poly[(vinyl pyrrolidone)-co-(mono-decyl maleate)] (PVPMDM 60/40, 72/25), and Poly[(vinyl pyrrolidone)-co-(di-decyl maleate)] 80/20 and Poly[(vinyl pyrrolidone)-co-(mono-eicosanoyl maleate)] 70/30 were synthesized in a similar way as poly[(vinyl pyrrolidone)-co-(octyl dodecyl maleate)] 80/20. However the purification was not done by washing with water and acetone, but by dissolving the precipitate formed during the synthesis in IPA (isopropyl alcohol). By subsequently adding the solution drop-wise into heptane, the copolymers precipitate from the solution. The copolymers were collected and dried.

The copolymers were analyzed with $^1$H-NMR and the monomer ratio in the copolymer calculated. The viscosities of the 5 wt % solutions of the copolymers in IPA were measured with a Viscolite VL7-100B-d15 of Hydramotion. The results are given in Table 1 below.

TABLE 1

| Copolymer | Monomer ratio in feed (wt %): | Monomer ratio in feed (mol %): | Monomer ratio in copolymer determined with 1H-NMR (wt %): | Vibrational Viscosity (cP) 5 wt % solution in IPA at 20° C. ± 1° C. |
|---|---|---|---|---|
| PVPM20-65:35 | 65:35 | 86.9:13.1 | 64.3:35.7 | 13 |
| PVPM20-80:20 | 80:20 | 93.4:6.6 | 81.5:18.5 | 11* |
| PVPM20-85:15 | 85:15 | 95.3:4.7 | 83.9:16.1 | 10 |
| PVPM20-90:10 | 90:10 | 97.0:3.0 | Not determined | Not determined |
| PVPMDM-60:40 | 60:40 | 77.6:22.4 | 60.8:39.2 | 16 |
| PVPMDM-75:25 | 75:25 | 87.4:12.6 | 74.9:25.1 | 12 |

TABLE 1-continued

| Copolymer | Monomer ratio in feed (wt %): | Monomer ratio in feed (mol %): | Monomer ratio in copolymer determined with 1H-NMR (wt %): | Vibrational Viscosity (cP) 5 wt % solution in IPA at 20° C. ± 1° C. |
|---|---|---|---|---|
| PVPMEM-70:30 | 70:30 | 89.3:10.7 | 70.1:29.9 | 11 |
| PVPDDM-80:20 | 80:20 | 93.4:6.6 | 79.1:20.9 | 15 |

\* PVPM20-80:20 ( Mn 23,918 and Mw 35,654 determined with GPC using PEG standards) results in a viscosity of 11 cP in this method

PVPM20

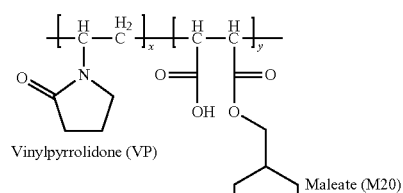

Vinylpyrrolidone (VP)  Maleate (M20)

PVPMDM

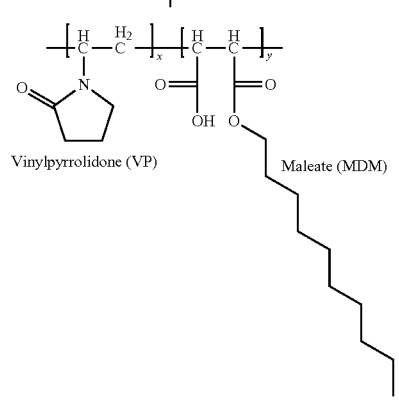

Vinylpyrrolidone (VP)  Maleate (MDM)

PVPDDM

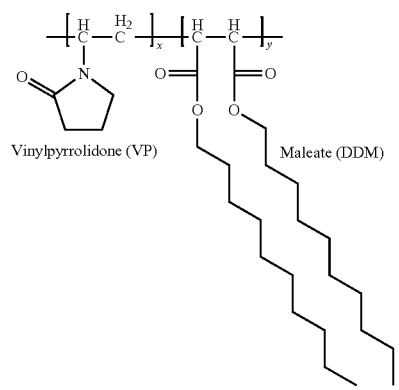

Vinylpyrrolidone (VP)  Maleate (DDM)

TABLE 1-continued

| Copolymer | Monomer ratio in feed (wt %): | Monomer ratio in feed (mol %): | Monomer ratio in copolymer determined with 1H-NMR (wt %): | Vibrational Viscosity (cP) 5 wt % solution in IPA at 20° C. ± 1° C. |
|---|---|---|---|---|
| PVPMEM | | | | |

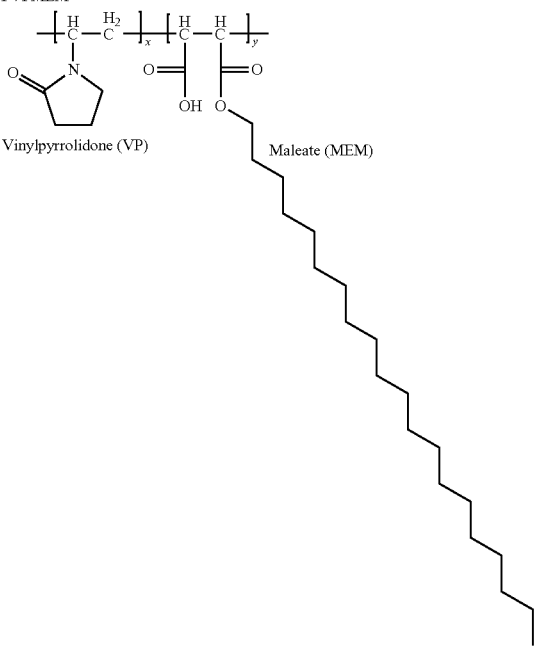

Vinylpyrrolidone (VP)   Maleate (MEM)

The different co-polymers (in short PVPM20, PVPMDM, PVPDDM and PVPMEM; see for the structures above) were dissolved to a final concentration of 2.5 wt % or 5 wt % in 2-propanol. The resulting copolymer solutions were then supplemented with different concentrations of BKC (Sigma Aldrich) or BEZ (Sigma Aldrich).

Co-Polymer Screening for Antimicrobial Activity

Antimicrobial activity screening was performed with an N-vinyl lactam copolymer obtainable by feeding a monomer mixture of VP and M20 at a 90% to 10% weight ratio, respectively, and supplemented with 0.1%, 0.5% or 1.0% BKC from a 50% (w/v) stock solution. PVPM20-90:10 without BKC, and BKC solutions of 0.1%, 0.5% or 1.0% without PVPM20 were used as controls. The different formulations were used to coat 96-well microtiter plates by applying different aliquots to the bottoms of the wells; 5 µl of the original 5% PVPM20 solutions, 2 µl and 5 µl of 0.5% PVPM20 solutions (10× diluted), and 2 µl and 5 µl of 0.05% PVPM20 solutions (100× diluted). The wells were air-dried, resulting in the deposition of a polymer film loaded with BKC on the bottom of the wells. The BKC controls were applied using the same approach. Next, 100 µl aliquots of a culture of exponentially growing S. aureus HG001 in TSB were added to the wells and growth was monitored for 14 hours by optical density readings at 600 nm ($OD_{600}$) using a Biotek powerwave plate reader at maximal shaking.

Disk Diffusion Assay

PVPM20-90:10 (5%) formulations with either 0.1%, 0.5% or 1% BKC were spotted in 5 µl aliquots on 5 mm Whatman® paper disks. Also, 5 µl aliquots of 0.1%, 0.5% or 1% BKC solutions were spotted on the disks. After disk drying at room temperature, the disks were placed on TSA plates onto which S. aureus HG001 had been spread to obtain a confluent lawn of cells. These plates were then incubated overnight at 37° C. and, the next day, the sizes of the observed inhibition zones were measured to estimate the diffusion of BKC from the paper disks.

S. aureus Contamination and Transmission Assay

To assay the impact of different polymer formulations on the contamination of surfaces with S. aureus and the subsequent S. aureus transmission to other surfaces, a dedicated assay was developed. Briefly, an overnight culture of S. aureus HG001 was diluted 1:10.000 and 1 ml was plated confluently onto two large bioassay plates with TSA. After inoculation, the plates were dried at 37° C. for approximately 30 min to allow bacteria to settle and to remove access moisture. Nitrile examination gloves were wrapped around self-fabricated stamps (FIGS. 3, A and B), which were made from absorption towel placed on a bottle cap and secured by a parafilm wrapping (FIG. 3A). The gloved stamps were coated with 50 µl polymer formulations, or they were left untreated (control). Contamination and transmission was achieved by pressing the gloved stamp (no. 1) onto the plate inoculated with S. aureus for approximately 10 sec (FIG. 3C). The stamp was then used to contaminate a second stamp (no. 2) by pressing the two together for 5 sec (FIG. 3D), after which it was pressed for 5 sec onto a clean TSA plate (FIG. 3F). Subsequently, the second stamp was first pressed against a third stamp (no. 3; FIG. 3E), and both stamps were then pressed onto clean TSA plates for 5 sec (FIG. 3F). All plates were incubated overnight at 37° C. Bacterial growth on the agar plates, including that on the two bio-assay plates used for the initial contamination of stamp no. 1, was used to assess the quality and anti-bacterial capacity of the polymer films applied to the stamps. Importantly, we included five non-coated control stamps, which were pressed onto different locations on the bioassay plates, to preclude a possible position-related assay bias.

BKC Release Assay

The different 5 wt % polymer formulations were supplemented with 0.45 wt % BKC and 20 µl coated to the first well of each row of a 96-well plate. After evaporation of the solvent (2-propanol), 100 µl of an aqueous BPB (BisPhenol Blue) solution ($25 \times 10^{-3}$ mmol/L) was added to the coated wells and the plate was incubated for 30 seconds at room temperature. Next, the aqueous phase was removed from the well and the formation of blue BPB-BKC complexes was assessed by visual inspection. This process was repeated until blue BPB-BKC complexes were no longer observed, and the number of repeated BPB incubation steps was recorded.

Glove Contamination Assay

Nitrile examination gloves (Sterling Nitrile Powder-Free Exam Gloves, Kimberly-Clark) were coated with 1 ml of PVPM20-80:20 (5 weight %) dissolved in 2-propanol and supplemented with 0.9% BKC. As a control, untreated nitrile examination gloves were used. Next, 13 volunteers were asked to wear a PVPM20-80:20 0.9% BKC-treated and an untreated examination glove (control), while performing their normal daily activities. To prevent a dominant hand bias, the coated glove was randomly assigned to the left or right hands of the volunteers. After ~3 hours, both gloved hands were pressed gently on a LB agar plate which was then incubated overnight at 37° C. Images were recorded with a G:BOX gel documentation and analysis system (Syngene). The numbers of CFUs on the plate were automatically assigned using the Syngene software package. CFU numbers thus determined were used as a measure for the numbers of microbial contaminants that had adhered to the glove.

Hand Contamination Assay

Both hands of a volunteer were first decontaminated with Sterillium. Next, the volunteer was asked to apply 1 ml of a PVPM20-80:20 0.9 weight % BKC solution onto one hand by hand rubbing, and, therefore, the other hand was protected from coating with a nitrile examination glove. After approximately 3 hours of normal daily activities, both hands were pressed gently on a LB agar plate. Upon overnight incubation of the plate at 37° C., the microbial contamination of the hands of the volunteers was assessed by CFU counting as described for the glove contamination assay.

BKC, BEZ and PHMBH+Cl— Release Assay (for Comparison)

PVPDDM-80:20 2.5 wt % formulations were supplemented with 0.45 wt % BKC or BEZ or PHMBH+Cl—) and 20 µl coated to the first well of each row of a 96-well plate. After evaporation of the 2-propanol solvent, 100 µl water was added to the coated wells and the plate was incubated for 60 seconds at room temperature. Next, the aqueous phase was removed from the well. This process was repeated 7 times. Subsequently 5 µl aqueous phase of each well was brought on TSA-plates, which were inoculated confluently with *S. aureus* HG001. After overnight incubation at 37° C. the plates were visually inspected for growth inhibition zones.

Example 1: The PVP-M20 Copolymer can Function as Coating-Carrier for Antimicrobial Agents This example describes the manufacture of a polymer film through a co-polymer formulation consisting of PVP and M20 (i.e. PVPM20). Co-polymers were prepared using a premixed monomer feed comprising different weight ratios of VP and M20. The different co-polymers (in short PVPM20) were dissolved to a final concentration of 5% in 2-propanol. The resulting PVPM20 solutions were then supplemented with different concentrations of BKC (Sigma Aldrich). The co-polymer antimicrobial activity screen was performed with a copolymer obtained using VP and M20, mixed at a 90% to 10% weight ratio (hereinafter: PVPM20-90:10), respectively, the copolymer being supplemented with 0.1%, 0.5% or 1.0% BKC from a 50% (w/v) stock solution.

PVPM20-90:10 without BKC, and BKC solutions of 0.1%, 0.5% or 1.0% without PVPM20 were used as controls. The different formulations were used to coat 96-well microtiter plates by applying different aliquots to the bottoms of the wells; 5 µl of the original 5% PVPM20 solutions, 2 µl and 5 µl of 0.5% PVPM20 solutions (10× diluted), and 2 µl and 5 µl of 0.05% PVPM20 solutions (100× diluted). The wells were air-dried, resulting in the deposition of a polymer film on the bottom of the wells. The BKC controls were applied using the same approach. Next, 100 µl aliquots of a culture of exponentially growing *S. aureus* HG001 (21) in TSB were added to the wells and growth was monitored for 14 hours by optical density readings at 600 nm ($OD_{600}$) using a Biotek powerwave plate reader at maximal shaking.

Coatings with the PVPM20 polymer, but without BKC had no effect on growth of *S. aureus* HG001 at 37° C. as the cells that were introduced into the wells with only PVPM20-90:10 showed comparable growth rates as cells introduced into the untreated wells (FIG. 1A). This showed that the polymer film itself has no antimicrobial activity. When supplementing the PVPM20-90:10 with 0.1 weight % BKC, the application of 5 µl of undiluted coating resulted in a complete inhibition of growth. However, when this formulation was diluted 10-fold, neither the 2 µl nor the 5 µl coatings were able to inhibit growth (FIG. 1B). By increasing the concentration of BKC to 0.5 weight % the growth-inhibiting power of the polymer formulation increased considerably. In this case, coatings of 2 µl and 5 µl of the 10-fold diluted PVPM20-90:10 with 0.5% BKC efficiently prevented growth of *S. aureus* (FIG. 1C). Growth inhibition was even further enhanced by using a PVPM20-90:10 formulation with 1.0 weight % BKC, where even the 5 µl coating of a 100-fold diluted formulation was sufficient to stop growth of *S. aureus* (FIG. 1D).

Example 2: The PVP-M20 Polymer System Acts as a Slow-Release Carrier for Antimicrobial Agents The observation that the PVPM20-90:10 polymer formulation slightly decreased the antimicrobial effects of BKC suggested that the polymer coating of the microtiter plate inhibited the release of BKC into the culture medium. This idea was tested in a disk diffusion assay using Tryptic Soy Agar (TSA) plates confluently inoculated with *S. aureus* HG001. After overnight incubation at 37° C., the growth inhibition zones around the paper disks were examined. Upon comparison of the growth inhibition zones around paper disks with PVPM20-90:10 plus BKC or with BKC alone, but both containing BKC at the same concentration, it was clearly evident that PVPM20-90:10 indeed inhibited the diffusion of BKC into the surrounding agar medium. Already at a BKC concentration of 0.1 weight % the PVPM20-90:10 polymer resulted in a substantial reduction of the inhibition zone (FIG. 2).

This inhibitory effect of PVPM20-90:10 on BKC diffusion became less prominent when higher concentrations of BKC were used. The latter observation can be explained by the higher concentration gradient of BKC in the PVPM20 relative to the surrounding agar medium, resulting in a faster release of the BKC and effectively more BKC that is available to diffuse from the paper disk into the surrounding agar medium. Alternatively, the PVPM20 coating may become saturated with BKC, allowing the BKC that is available in excess to diffuse rapidly from the paper disk into the surrounding agar medium. The fact that PVPM20-90:10 can set a limit to the diffusion of BKC into the surrounding medium implies that PVPM20 can represent an attractive slow-release carrier for antimicrobial compounds, such as BKC. In turn, this made the formulation an attractive candidate for further proof-of-principle studies on the antimicrobial microglove concept.

Example 3: The Antimicrobial PVP-M20 System Effectively Prevents S. aureus Transmission In the initial experiments described above, VP and M20 were used as premix at a 90% to 10% weight ratio to prepare the copolymer. To evaluate the resulting VP:M20 ratio in the copolymer as a parameter for the properties of the copolymer film that is to represent a microglove, three different copolymers were synthesized using premixed monomer feeds with different VP:M20 weight ratios, namely 90:10 (PVPM20-90:10), 85:15 (PVPM20-85:15), and 80:20 (PVPM20-80:20).

To assay the impact of different copolymer formulations on the contamination of surfaces with S. aureus and the subsequent S. aureus transmission to other surfaces, a dedicated assay was developed. Briefly, an overnight culture of S. aureus HG001 was diluted 1:10.000 and 1 ml was plated confluently onto two large bioassay plates with TSA. After inoculation, the plates were dried at 37° C. for approximately 30 min to allow bacteria to settle and to remove access moisture. Nitrile examination gloves were wrapped around self-fabricated stamps (FIGS. 3, A and B), which were made from absorption towel placed on a bottle cap and secured by a parafilm wrapping (FIG. 3A). The gloved stamps were coated with 50 µl polymer formulations, or they were left untreated (control). Contamination and transmission was achieved by pressing the gloved stamp (no. 1) onto the plate inoculated with S. aureus for approximately 10 sec (FIG. 3C). The stamp was then used to contaminate a second stamp (no. 2) by pressing the two together for 5 sec (FIG. 3D), after which it was pressed for 5 sec onto a clean TSA plate (FIG. 3F). Subsequently, the second stamp was first pressed against a third stamp (no. 3; FIG. 3E), and both stamps were then pressed onto clean TSA plates for 5 sec (FIG. 3F). All plates were incubated overnight at 37° C. Bacterial growth on the agar plates, including that on the two bio-assay plates used for the initial contamination of stamp no. 1, was used to assess the quality and anti-bacterial capacity of the polymer films applied to the stamps. Importantly, we included five non-coated control stamps, which were pressed onto different locations on the bioassay plates, to preclude a possible position-related assay bias.

This in-house developed contamination and transmission assay convincingly demonstrated that, using the non-coated control stamps, transmission of S. aureus HG001 was detectable from the initially contaminated stamp to both the second and third stamps (FIG. 4). The numbers of transmitted bacteria decreased visibly after each transfer. Furthermore, the imprints left by the control stamps on the inoculated bioassay plate that was used for stamp contamination showed only the outline of the stamps and, as expected, there was no inhibition of bacterial growth.

When stamps were coated with the original PVPM20-90: 10 formulation containing 0.1% BKC (FIG. 5A), contamination of the first stamp was slightly reduced compared to the uncoated control stamps. The imprint on the bioassay plate showed a small clearing zone, which suggests that part of the polymer coating was released upon contact with the agar. This can be explained by the fact that BKC residing in the polymer coating will diffuse into the agar, resulting in the clearing zones in which bacterial growth is inhibited. Increasing the concentration of BKC to 0.3% (FIG. 5A) prevented transmission to stamps no. 2 and no. 3, and even stamp no. 1 did not transmit viable bacteria, suggesting that the antibacterial coating was successfully applied. However, the imprint on the bioassay plate was characterized by a large clearing zone (FIG. 5A). This is likely due to the diffusion of BKC, which implies the release of some of the polymer film applied to the stamp.

Increasing the BKC concentration to 0.5%, 1%, 2% or 5% resulted in even larger clearing zones (FIG. 5A), presumably as a direct consequence of increasing the BKC concentration. Upon changing the VP/M20 weight ratio to 85%/15% (i.e. PVPM20-85:15), the addition of 0.1% BKC did not prevent the contamination of stamps no. 2 and no. 3 (FIG. 5B). Increasing the BKC concentration to 0.3%, which proved to be effective when using the PVPM20-90:10 formulation, clearly reduced the number of transmitted bacteria although it was not sufficient to fully prevent transmission to stamp no. 3. (FIG. 5B). Applying PVPM20-85:15 with a BKC concentration of 0.5% prevented bacterial transmission to stamp no. 2 and no. 3. When the BKC concentration was increased to 1% and higher, none of the stamps showed contamination. However, the large clearing zones on the inoculated bioassay plate were indicative for the release of the polymer film obtained when VP/M20 were present in the monomer mixture at a ratio of 80%/20%, (i.e. PVPM20-80:20). The coating of the stamps with PVPM20-80:20 containing 0.3% BKC resulted in a substantial reduction of S. aureus HG001 transmission, although it was not completely prevented. Importantly, in this case, no clearing zones were detectable on the inoculated bioassay plate used to start the transmission experiment (FIG. 5C). Increasing the BKC concentration to 0.5% completely abolished the contamination of all three stamps, again without generating a clearing zone on the inoculated bioassay plate (FIG. 5C).

These findings indicate that, while the polymer film remained intact on the stamp, it was able to prevent stamp contamination with bacteria and their subsequent transmission. PVPM20-80:20 polymer films containing BKC concentrations of 1% or more released substantial amounts of BKC onto the inoculated bioassay plate, as reflected by large clearing zones (FIG. 5C). Based on the significant antimicrobial activity of the PVPM20-80:20 supplemented with 0.5% BKC, and on the stable film that it forms, the PVPM20-80:20 formulation was selected for further testing.

Example 4: The PVP-M Coating Facilitates Slow Biocide Release

The slow release properties of the PVPM20, PVPMDM, PVPMEM and PVPDDM co-polymer formulations were verified in a BKC and a BEZ release test that were performed in 96-well plates. The different polymer formulations (i.e. PVPM20-85:15, PVPM20-80:20, PVPM20-65:35, PVPMDM-60:40, PVPMDM-75:25, PVPMEM-80:20 and PVPDDM-80:20 in 2-propanol at 2.5 wt % were supplemented with 0.45 wt % BKC or BEZ. 20 μl was coated to the first well of each row of a 96-well plate. After evaporation of the 2-propanol solvent, 100 μl of an aqueous BPB solution (25×10$^{-3}$ mmol/L) was added to the coated wells and the plate was incubated for 30 seconds at room temperature. BPB forms a blue complex with free BKC and free BEZ when it is released from the polymer film into an aqueous solution. Of note, the BPB-BKC or BPB-BEZ complex is blue, whereas the BPB solution itself is purple (20). Next, the aqueous phase was removed from the well and the formation of blue BPB-BKC or BPB-BEZ complexes was assessed by visual inspection. This process was repeated until blue BPB-BKC complexes were no longer observed, and the number of repeated BPB incubation steps was recorded.

The number of cycles needed to release readily detectable amounts of BKC or BEZ was used as a measure to assess the BKC-retaining or BEZ-retaining properties of the different polymer formulations.

The polymer film in the first well made with the PVPM20-65:35 formulation and that of the PVPMEM-70:30 formulation broke in small pieces after contact with water. These copolymers apparently are too hydrophobic for homogenously encapsulating BKC and BEZ, the particular biocides subject of this example. The enlarged BKC and/or BEZ domains so formed rapidly disrupt the films upon dissolving in contact with water. The test was stopped after one incubation cycle for these formulations. The PVPMDM-60:40 formulation did not release BKC or BEZ in 30 seconds in contact with BPB solution, because of a too slow release.

The PVPM20-80:20 formulation, the PVPM20-85:15 formulation and the PVPMDM-75:25 formulation were very efficient in releasing BKC or BEZ from the film as it took up to 7-8 consecutive incubations with the aqueous BPB solution until BKC or BEZ was no longer detectably released. The test showed that the PVPDDM-80:20 formulation was far most efficient in releasing BKC as well as BEZ from the film as it took up to 11 consecutive incubations with the aqueous BPB solution until BKC or BEZ was no longer detectably released.

Additionally and as reference, we tested the BKC and the BEZ release from a 0.45% BKC and 0.45% BEZ coating without PVPM20-80:20. In this case, all coated material dissolved instantaneously upon addition of the BPB solution and all BKC was thereby released. Of note, the BKC or BEZ concentration in commercially available formulations is lower (~0.2%) than the concentration used in our present polymer formulations. However, the BKC-release assay and BEZ-release assay shows that by using BKC or BEZ in combination with the copolymers PVPM20-80:20, PVPMDM-75:25 and PVPDDM-80:20, the actual release of free BKC or BEZ from the polymer film is considerably lower than that of unaided BKC or BEZ as implemented in commercial BKC- and BEZ-based disinfectants.

Combined with the other data presented above, it can thus be concluded that the high concentration of microbial agent is retained within the PVPM20-80:20, PVPMDM-75:25 and PVPDDM-80:20 copolymer film and that is only slowly released upon contact with water. This slow release combined with the good film properties demonstrates that the formulation meets the basic requirements for a hand rub that facilitates the establishment of an antimicrobial microglove.

A PVPMEM-80:20 formulation was not prepared, however studying the results and observing the trends it is conceivable that PVPMEM-80:20 will also give good slow release properties upon contact with water An overview of the results are given in Table 2 below.

TABLE 2

| Copolymer | Monomer ratio in feed (wt %): | Film breaks | Test1 (BKC) | Test2 (BEZ) |
|---|---|---|---|---|
| PVPM20-65:35 | 65:35 | yes | Film breaks | ND |
| PVPM20-80:20 | 80:20 | no | 7x | 7x |
| PVPM20-85:15 | 85:15 | no | 7x | ND |
| PVPMDM-60:40 | 60:40 | yes | No release | ND |
| PVPMDM-75:25 | 75:25 | no | 8x | ND |
| PVPMEM-70:30 | 70:30 | yes | Film breaks | ND |
| PVPDDM-80:20 | 80:20 | no | 11x | 11x |
| BKC only | NA | NA | 1x | NA |
| BEZ only | NA | NA | NA | 1x |

Figure 6:
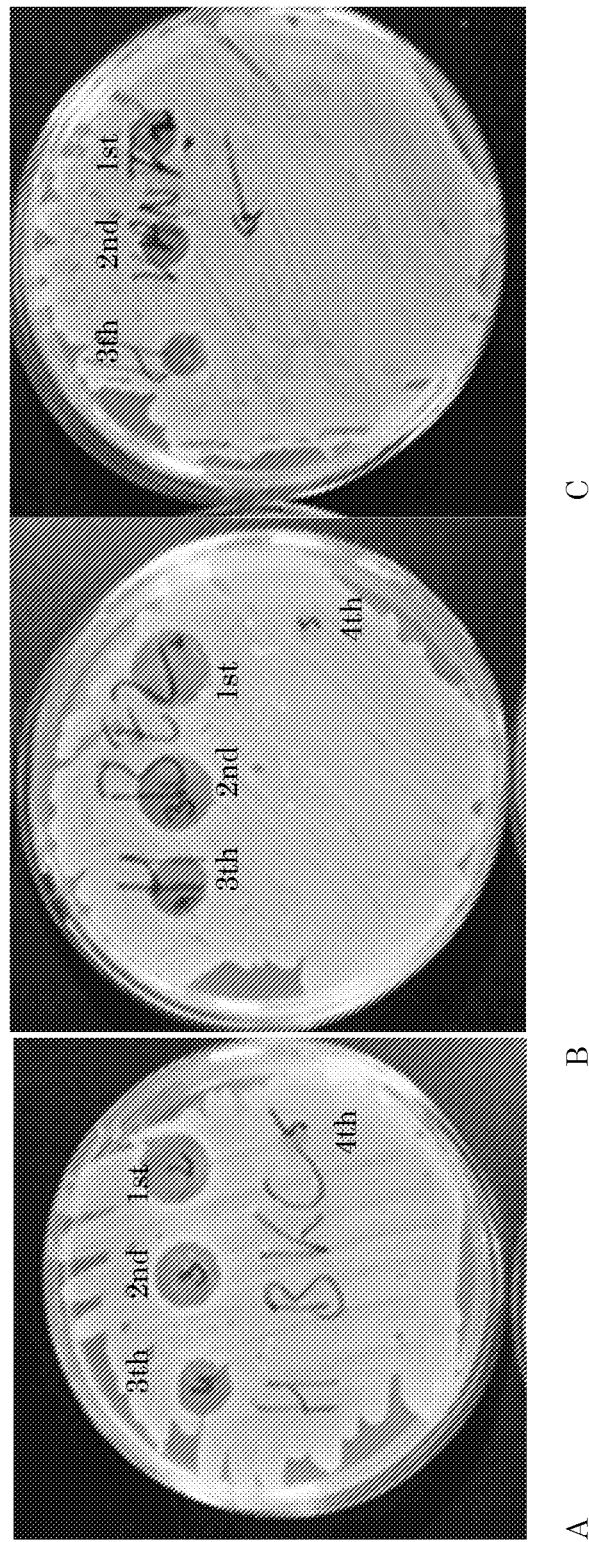

Test1: Biocide BKC: Number of incubations after which BKC was no longer detectable
Test2: Biocide BEZ: Number fo incubations after which BEZ was no longer detectable
ND = not determined
NA = not applicable Example 5: Copolymer PVP-DDM-80:20 Facilitates Slow Release of Different Types of Biocides Exemplary N-vinyl lactam copolymer of the invention PVPDDM-80:20 at 2.5 wt % in 2-propanol was supplemented with 0.45 wt % of the bactericidal agent BKC, BEZ or PHMBH+Cl—. Twenty μl was coated to the first well of each row of a 96-well plate. After evaporation of the solvent, 100 μl of water was added to the coated wells and the plate was incubated for 1 minute at room temperature. Next, the aqueous phase was removed from the well. This process was repeated 7 times. Depending on the degree of interaction with the polymer matrix, biocide will be slowly released to a certain extent into water during incubation. Five μl of each incubation step was brought on TSA-plates which were inoculated confluently with *S. aureus* HG001. After overnight incubation at 37° C. the plates were visually inspected for growth inhibition zones. The number of cycles after which growth inhibition was observed were 4, 4 and 3 for the formulations supplemented with BKC, BEZ, or PHMBH+Cl—) respectively (see also FIG. 6).

Example 6: Validation of the Antimicrobial Microglove Concept

This example shows that the PVPM20-80:20 0.9% BKC formulation can function as a microglove that offers protection against microbial contamination, as was demonstrated using a glove contamination assay.

Nitrile examination gloves (Sterling Nitrile Powder-Free Exam Gloves, Kimberly-Clark) were coated with 1 ml of an antimicrobial composition comprising PVPM20-80:20 (5 weight %) dissolved in 2-propanol and supplemented with 0.9% BKC. As a control, untreated nitrile examination gloves were used. Next, 13 volunteers were asked to wear on one hand a treated (coated) glove and on the other hand an untreated examination glove (control), while performing their normal daily activities. To prevent a dominant hand bias, the coated glove was randomly assigned to the left or right hands of the volunteers. After ~3 hours, both gloved hands were pressed gently on a LB agar plate which was then incubated overnight at 37° C. Images were recorded with a G:BOX gel documentation and analysis system (Syngene). The numbers of CFUs on the plate were automatically assigned using the Syngene software package.

CFU numbers thus determined were used as a measure for the numbers of microbial contaminants that had adhered to the glove.

As shown in FIG. 7, the gloves coated with the antimicrobial composition yielded significantly lower numbers of CFUs on the inner hand surface than the non-coated gloves (FIG. 7A), demonstrating a protective antimicrobial effect of the polymer coating (FIG. 7B). Overall, the numbers of CFUs were approximately halved when a glove was treated with antimicrobial composition, but in some individual experiments the effect was substantially more prominent with up to 40-fold reductions in CFUs. In each single experiment the coating of a glove led to a reduced number of microbial contaminants compared to the respective control (FIG. 7B).

Since the surface of a nitrile examination glove only mimics the situation on the human skin, we decided to test the microglove concept on the hands of three volunteers, which was acceptable since the components of the antimicrobial composition can be considered as safe based on the well-known biocompatibility of PVP polymers.

Both hands of a volunteer were first decontaminated with an alcohol based handrub (Sterillium®). Next, the volunteer was asked to apply 1 ml of a PVPM20-80:20 0.9% BKC solution onto one hand by hand rubbing, and, therefore, the other hand was protected from coating with a nitrile examination glove. To prevent a dominant hand bias, the coated glove was randomly assigned to the left or right hands of the volunteers. Thus, for each volunteer one hand was treated with the polymer formulation, while the other hand remained untreated. After approximately 3 hours of normal daily activities, both hands were pressed gently on a LB agar plate. Upon overnight incubation of the plate at 37° C., the microbial contamination of the hands of the volunteers was assessed by CFU counting as described for the glove contamination assay.

This analysis revealed that hands coated with the polymer-based formulation showed a significant reduction in CFU counts (FIG. 8). For the non-treated hands an average of 301 CFUs was counted, while the coated hands carried on average 52 CFUs. This six-fold reduction in microbial contamination shows that the microglove concept has indeed a considerable protective effect against newly acquired contaminants for a period of at least approximately 3 hours. Importantly, we observed that the effect of the coating was even more effective on the hands of volunteers than on examination gloves.

REFERENCES 1. de Kraker, M. E., Davey, P. G., Grundmann, H.; BURDEN study group. (2011) Mortality and hospital stay associated with resistant *Staphylococcus aureus* and *Escherichia coli* bacteremia: Estimating the burden of antibiotic resistance in europe. *PLoS Med.*, 8, e1001104
2. Parvizi, J., Pawasarat, I. M., Azzam, K. A., Joshi, A., Hansen, E. N. and Bozic, K. J. (2010) Periprosthetic joint infection: The economic impact of methicillin-resistant infections. *J. Arthroplasty*, 25, 103-107.
3. de Kraker, M. E., Wolkewitz, M., Davey, P. G., Koller, W., Berger, J., Nagler, J., Icket, C., Kalenic, S. et al. (2011) Clinical impact of antimicrobial resistance in european hospitals: Excess mortality and length of hospital stay related to methicillin-resistant *Staphylococcus aureus* bloodstream infections. *Antimicrob. Agents Chemother.*, 55, 1598-1605.
4. de Kraker, M. E., Wolkewitz, M., Davey, P. G., Koller, W., Berger, J., Nagler, J., Icket, C., Kalenic, S. et al. (2011) Burden of antimicrobial resistance in european hospitals: Excess mortality and length of hospital stay associated with bloodstream infections due to *Escherichia coli* resistant to third-generation cephalosporins. *J. Antimicrob. Chemother.*, 66, 398-407.
5. Ciccolini, M., Donker, T., Grundmann, H., Bonten, M. J. and Woolhouse, M. (2014) Efficient surveillance for healthcare-associated infections spreading between hospitals. *Proc. Natl. Acad. Sci. U.S.A.*, 111, 2271-2276.
6. Donker, T., Wallinga, J. and Grundmann, H. (2014) Dispersal of antibiotic-resistant high-risk clones by hospital networks: Changing the patient direction can make all the difference. *J. Hosp. Infect.*, 86, 34-41.
7. Pittet, D., Allegranzi, B., Sax, H., Dharan, S., Pessoa-Silva, C. L., Donaldson, L. and Boyce, J. M. (2006) Evidence-based model for hand transmission during patient care and the role of improved practices. *Lancet Infect. Dis.*, 6, 641-652.
8. Ciccolini, M., Donker, T., Köck, R., Mielke, M., Hendrix, R., Jurke, A., Rahamat-Langendoen, J., Becker, K., et al. (2013) Infection prevention in a connected world: The case for a regional approach. *Int. J. Med. Microbiol.*, 303, 380-387.
9. Kretzer, E. K. and Larson, E. L (1998) Behavioral interventions to improve infection control practices. *Am. J. Infect. Control*, 26, 245-253.
10. Curtis, V. and Carincross, S. (2003) Effect of washing hands with soap on diarrhoea risk in the community: A systematic review. *Lancet Infect Dis*, 3, 275-281.
11. WHO. (2000) World health report 2000.
12. Pittet, D. (2001) Compliance with hand disinfection and its impact on hospital-acquired infections. *J. Hosp. Infect.*, 48, 40-46.
13. Allegranzi, B. and Pittet, D. (2009) Role of hand hygiene in healthcare-associated infection prevention. *J. Hosp. Infect.*, 73, 305-315.
14. Randle, J., Arthur, A. and Vaughan, N. (2010) Twenty-four-hour observational study of hospital hand hygiene compliance. *J. Hosp. Infect.*, 76, 252-255.
15. Larson, E. and Killien, M. (1982) Factors influencing handwashing behavior of patient care personnel. *Am. J. Infect. Control*, 10, 93-99.
16. Steere, A. C. and Mallison, G. F. (1975) Handwashing practices for the prevention of nosocomial infections. *Ann. Intern. Med.*, 83, 683-690.
17. Ulmer, H. W. and Flipsen, T. A. (2014) Maleate-based copolymers and methods for preparing the same. WO2011/002278
18. Patarca, R., Rosenzwei, J. A., Zuniga, A. A., and Fletcher, M. A. (2000) Benzalkonium salts: Effects on G protein-mediated processes and surface membranes. *Crit. Rev. Oncog.*, 11, 255-305.
19. Basketter, D. A., Marriott, M., Gilmour, N. J. and White, I. R. (2004-4) Strong irritants masquerading as skin allergens: The case of benzalkonium chloride. *Contact Derm.*, 50, 213-217.
20. Yamamoto, K. (1995) Sensitive determination of quaternary ammonium salts by extraction-spectrophotometry of ion associates with bromophenol blue anion and coextraction. *Anal. Chim. Acta.*, 302, 75-79.
21. Herbert, S., Ziebandt, A. K., Ohlsen, K., Schäfer, T., Hecker, M., Albrecht, D., Novick, R. and Götz, F. (2010) Repair of global regulators in *Staphylococcus aureus* 8325 and comparative analysis with other clinical isolates. *Infect. Immun.*, 78, 2877-2889.

The invention claimed is:

1. An antimicrobial composition comprising an antimicrobial agent, a pharmaceutically acceptable carrier material, and an N-vinyl lactam copolymer,
   wherein said copolymer is obtained by solution polymerization of vinyl pyrrolidone monomer units (A) and hydrophobically derivatized maleate monomer units (B) selected from mono-eicosanoyl maleate, octyl-dodecyl-maleate, mono-decyl maleate, and di-decyl maleate,
   wherein said polymerization comprises continuously feeding of a monomer mixture comprising:
   85 weight percent of monomer (A) and 15 weight percent of mono-eicosanoyl maleate,
   70-90 weight percent of monomer (A) and 10-30 weight percent of di-decyl maleate,
   70-75 weight percent of monomer (A) and 25-30 weight percent of mono-decyl maleate, or
   80-90 weight percent of monomer (A) and 10-20 weight percent of octyl-decyl maleate over a predetermined period of time to a reaction vessel.

2. The antimicrobial composition according to claim 1, wherein the N-vinyl lactam copolymer is present in said composition at a concentration of about 0.5-10 weight percent.

3. The antimicrobial composition according to claim 1, wherein the concentration of antimicrobial agent is between about 0.01 and 2 weight percent.

4. The antimicrobial composition according to claim 1, wherein said antimicrobial agent is selected from the group consisting of quaternium salts, phenols, halogen-releasing compounds, aldehydes, biguanides, polymeric biguanides, amphoterics, iodine-based compounds, peroxygen-based compounds, and silver-containing compounds.

5. The antimicrobial composition according to claim 4, wherein the antimicrobial agent is a quaternary ammonium compound selected from the group consisting of benzethonium chloride, benzalkonium or benzethonium bromide or fluoride, cetyl pyridinium chloride, dequalinium chloride, N-myristyl-N-methyl-morpholinium methyl sulfate, poly[N-[3-(dimethylammonio)propyl]-N'-[3-(ethyleneoxyethylene dimethylammoinio)propyl]urea dichloride], alpha-4-[1-tris(2-hydroxyethyl)ammonium chloride-2-butenyl]-omega-tris(2-hydroxyethyl)ammonium chloride, and poly[oxyethylene (dimethyliminio)ethylene (dimethyliminio)-ethylene dichloride].

6. The antimicrobial composition according to claim 1, wherein the pharmaceutically acceptable carrier material is an alcohol, water, an ester, a skin care oil, an emulsifier, emollient, or any mixture thereof.

7. A method for reducing or eliminating the number of micro-organisms on a surface, comprising applying an antimicrobial composition according to claim 1 to said surface and allowing the formation of an antimicrobial film.

8. The method according to claim 7, wherein said surface is the surface of skin, hair and/or nails, or wherein the surface is the surface of a medical device or a personal care product.

9. The method according to claim 7, wherein said micro-organisms are bacteria, viruses, fungi, spores or yeast.

10. A product comprising a composition according to claim 1, the product selected from a skin sanitizer, hand-rub, or (micro)glove.

11. A slow-release carrier for an antimicrobial agent in an antimicrobial film or coating comprising N-vinyl lactam copolymer,
    wherein said copolymer is obtained by solution polymerization of vinyl pyrrolidone monomer units (A) and hydrophobically derivatized maleate monomer units (B) selected from mono-eicosanoyl maleate, octyl-dodecyl-maleate, mono-decyl maleate, and di-decyl maleate,
    wherein said polymerization comprises continuously feeding of a monomer mixture to a reaction vessel comprising:
    85 weight percent of monomer (A) and 15 weight percent of mono-eicosanoyl maleate,
    70-90 weight percent of monomer (A) and 10-30 weight percent of di-decyl maleate,
    70-75 weight percent of monomer (A) and 25-30 weight percent of mono-decyl maleate, or
    80-90 weight percent of monomer (A) and 10-20 weight percent of octyl-decyl maleate, over a predetermined period of time to a reaction vessel.

12. The antimicrobial composition according to claim 1, wherein the copolymer is obtained by polymerization comprising the continuously feeding of a monomer mixture comprising vinyl pyrrolidone and octyl-dodecyl-maleate in a weight ratio of 80:20.

13. The antimicrobial composition according to claim 1, wherein the copolymer is obtained by polymerization comprising the continuously feeding of a monomer mixture comprising vinyl pyrrolidone and octyl-dodecyl-maleate in a weight ratio of 85:15.

14. The antimicrobial composition according to claim 1, wherein the copolymer is obtained by polymerization comprising the continuously feeding of a monomer mixture comprising vinyl pyrrolidone and mono-decyl maleate in a weight ratio of 75:25.

15. The antimicrobial composition according to claim 1, wherein the copolymer is obtained by polymerization comprising the continuously feeding of a monomer mixture comprising vinyl pyrrolidone and di-decyl maleate in a weight ratio of 80:20.

16. The antimicrobial composition according to claim 1, wherein said polymerization comprises the continuously feeding of a monomer mixture comprising 70-90 weight percent of monomer (A) and 10-30 weight percent of di-decyl maleate.

17. The antimicrobial composition according to claim 1, wherein the copolymer is obtained by polymerization comprising the continuously feeding of a monomer mixture comprising 70-75 weight percent of monomer (A) and 25-30 weight percent of mono-decyl maleate.

18. The antimicrobial composition according to claim 1, wherein the copolymer is obtained by polymerization comprising the continuously feeding of a monomer mixture comprising 80-90 weight percent of monomer (A) and 10-20 weight percent of octyl-decyl maleate.

19. The antimicrobial composition according to claim 1, wherein the copolymer is obtained by polymerization comprising the continuously feeding of a monomer mixture comprising 85 weight percent of monomer (A) and 15 weight percent of mono-eicosanoyl maleate.

* * * * *